(12) United States Patent
Aissaoui et al.

(10) Patent No.: US 8,329,706 B2
(45) Date of Patent: Dec. 11, 2012

(54) OXAZOLIDINONE DERIVATIVES

(75) Inventors: Hamed Aissaoui, Pulversheim (FR); Christoph Boss, Allschwil (CH); Christine Brotschi, Allschwil (CH); Markus Gude, Allschwil (CH); Romain Siegrist, Allschwil (CH); Thierry Sifferlen, Wentzwiller (FR); Jodi T Williams, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/319,780

(22) PCT Filed: May 11, 2010

(86) PCT No.: PCT/IB2010/052068
§ 371 (c)(1),
(2), (4) Date: Jan. 9, 2012

(87) PCT Pub. No.: WO2010/131192
PCT Pub. Date: Nov. 18, 2010

(65) Prior Publication Data
US 2012/0101111 A1    Apr. 26, 2012

(30) Foreign Application Priority Data

May 12, 2009 (WO) ............... PCT/IB2009/051949

(51) Int. Cl.
| | |
|---|---|
| *A61K 31/497* | (2006.01) |
| *A61K 31/4439* | (2006.01) |
| *A61K 31/428* | (2006.01) |
| *A61K 31/421* | (2006.01) |
| *C07D 413/02* | (2006.01) |
| *C07D 417/02* | (2006.01) |
| *C07D 263/18* | (2006.01) |

(52) U.S. Cl. ............. 514/255.05; 514/340; 514/367; 514/376; 544/405; 546/271.4; 548/152; 548/225

(58) Field of Classification Search ............... 514/376, 514/340, 274; 548/225; 546/271.4; 544/315
See application file for complete search history.

(56) References Cited

FOREIGN PATENT DOCUMENTS
WO    WO 2006/127550    11/2006

OTHER PUBLICATIONS

"Autism," [retrieved on May 14, 2008]. Retrieved online via Internet, URL: http://www.nlm.nih.gov/medlineplus/autism.html.*
"Anxiety," [retrieved on May 14, 2008]. Retrieved online via Internet, URL: http://www.nlm.nih.gov/medlineplus/anxiety.html.*
Caj, J. et al., "Antagonists of the orexin receptors", Expert Opinion on Therapeutic Patents, Informa Healthcare, GB LNKD-DOI: 10.1517/13543776.16.5.631, vol. 16, No. 5, May 1, 2006, pp. 631-646, XP002458093.

* cited by examiner

*Primary Examiner* — Kristin Bianchi
(74) *Attorney, Agent, or Firm* — Hoxie & Associates LLC

(57) ABSTRACT

The present invention relates to oxazolidinone derivatives of formula (I) wherein Y, $R^3$ and $R_4$ are as described in the description, to their preparation, to pharmaceutically acceptable salts thereof, and to their use as pharmaceuticals, to pharmaceutical compositions containing one or more compounds of formula (I), and especially to their use as orexin receptor antagonists.

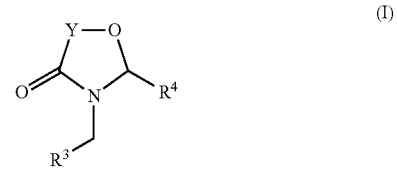

(I)

15 Claims, No Drawings

OXAZOLIDINONE DERIVATIVES

CROSS REFERENCE TO RELATED APPLICATIONS

This application is a U. S. Application under 35 U.S.C. 371 claiming benefit of PCT Application No. PCT/IB2010/052068, filed on May 11, 2010, which claims the benefit of PCT Application No. PCT/IB2009/051949, filed on May 12, 2009, the contents of each of which are incorporated herein by reference.

The present invention relates to novel oxazolidinone derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451). Furthermore, in vitro and in vivo evidence for a critical role of orexin signaling in the ventral tegmental area in neural plasticity relevant to addiction has been published (S. L. Borgland et al. Neuron, 2006, 49, 589-601).

Thus, orexin receptors may have numerous implications in pathologies as known from the literature, such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions. The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548) is currently in clinical development for primary insomnia. In the rat, the compound has been shown for example to decrease alertness, characterized by decreases in both active wake and locomotion; and to dose-dependently increase the time spent in both REM and NREM sleep (F. Jenck et al., Nature Medicine 2007, 13, 150-155). The compound has also been shown to enhance memory function in a rat model (WO2007/105177) and is also active in a rat model of post-traumatic stress disorder (WO2009/047723).

The present invention provides novel oxazolidinone derivatives, which are non-peptide antagonists of human orexin receptors. These compounds are in particular of potential use in the treatment of diseases related to the orexin system, especially comprising all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

1) A first aspect of the invention consists of compounds of the formula (I)

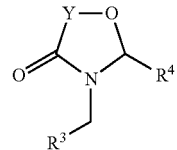

Formula (I)

wherein
Y represents $CH_2$, $CHR^1$, or $CR^1R^2$; wherein $R^1$ and $R^2$ independently represent $(C_{1-4})$alkyl;
$R^3$ represents $Ar^1$ or $Ar^3$—Z—$Ar^2$—* wherein the asterisk indicates the bond that is attached to the rest of the molecule; wherein
  $Ar^1$ represents aryl or heteroaryl, wherein the aryl or heteroaryl is independently unsubstituted, or mono-, di-, or tri-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, $(C_{1-3})$fluoroalkyl-thio-, and $(C_{3-6})$cycloalkyl-$(C_{1-4})$alkoxy;
  $Ar^2$ represents phenyl or 5- to 6-membered heteroaryl;
  Z represents a bond, O, or —$CH_2$—O—* wherein the asterisk indicates the bond that is attached to $Ar^2$;
  $Ar^3$ represents phenyl or 5- to 6-membered heteroaryl wherein the phenyl or 5- to 6-membered heteroaryl is independently unsubstituted, or mono-, di-, or tri-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy (notably substituents are selected from $(C_{1-4})$alkyl, $(C_{1-4})$alkoxy, and $(C_{1-3})$fluoroalkyl); and
$R^4$ represents aryl or heteroaryl, wherein the aryl or heteroaryl is independently mono-, di-, or tri-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, hydroxy-$(C_{1-4})$alkoxy, and $(C_{1-4})$alkoxy-$(C_{1-4})$alkoxy; wherein, in the specific case wherein said aryl or heteroaryl is a bicyclic ring, the aryl or heteroaryl may also be unsubstituted;
with the exception of the following compounds:
2-(2-bromophenyl)-3-[(4-methoxyphenyl)methyl]-4-oxazolidinone (CAS 199939-14-5);
2-(2-bromophenyl)-3-{[4-(trifluoromethyl)phenyl]methyl}-4-oxazolidinone (CAS 199939-13-4);
2-(2-bromophenyl)-3-(phenylmethyl)-4-oxazolidinone (CAS 199939-09-8); and
2-(4-methoxyphenyl)-3-[(4-methoxyphenyl)methyl]-5-methyl-4-oxazolidinone (CAS 84711-84-2).

The latter compounds are known from L. Giraud, E. Lacote, P. Renaud; "Preparation of 2-arylbenzaldehyde derivatives via free-radical ipso-substitution of an amidomethyl group" Helv. Chim. Acta (1997), 80(7), 2148-2156; and H. Aoyama, M. Sakamoto, K. Kuwabara, K. Yoshida, Y. Omote; "Photochemical reactions of .alpha.-oxo amides. Norrish type II reactions via zwitterionic intermediates" J. Am. Chem. Soc. (1983), 105(7), 1958-64.

In this patent application, a bond interrupted by a wavy line shows the point of attachment of the radical drawn. For example, the radical drawn below

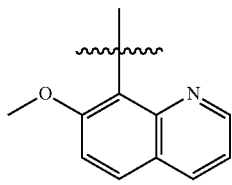

is the 7-methoxy-quinolin-8-yl group.

The term "halogen" means fluorine, chlorine, or bromine, preferably fluorine or chlorine.

The term "alkyl", used alone or in combination, refers to a saturated straight or branched chain alkyl group containing one to four carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of $(C_{1-4})$alkyl groups are methyl, ethyl, propyl, isopropyl, n-butyl, isobutyl, sec.-butyl and tert.-butyl. Preferred are methyl and ethyl. Most preferred is methyl. For the substituents $R^1$ and $R^2$ preferred is methyl. For the substituent $R^{15}$ representing a $(C_{1-4})$alkyl group, preferred are ethyl, n-propyl and especially isopropyl.

The term "cycloalkyl", used alone or in combination, refers to a saturated cyclic alkyl group containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of $(C_{3-6})$alkyl groups are cyclopropyl, cyclobutyl, cyclopentyl and cyclohexyl. Preferred is cyclopropyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert.-butoxy. Preferred are ethoxy and especially methoxy. For substituents of $R^4$ preferred examples are ethoxy and methoxy. For substituents of $Ar^1$ representing a phenyl group preferred examples are methoxy, ethoxy and especially isopropoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl. For the substituent $R^{15}$ preferred examples are trifluoromethyl, difluoromethyl, 2-fluoroethyl, 2,2-difluoroethyl and 2,2,2-trifluoroethyl (notably trifluoromethyl, difluoromethyl, and 2,2,2-trifluoroethyl).

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

The term "aryl", alone or in combination, means a phenyl or a naphthyl group. In addition, the term aryl also comprises phenyl rings fused to a 5- or 6-membered saturated or partially unsaturated non-aromatic ring optionally containing 1 to 2 oxygen atoms. Examples of aryl groups are phenyl, naphthyl, indanyl, tetrahydronaphthyl, benzo[1,3]dioxolyl, 2,3-dihydrobenzofuranyl, 2,3-dihydro-benzo[1,4]dioxinyl, chromanyl, and chromenyl. In a sub-embodiment, examples are phenyl, naphthyl, indanyl, benzo[1,3]dioxolyl, 2,3-dihydrobenzofuranyl, and 2,3-dihydro-benzo[1,4]dioxinyl. In another sub-embodiment examples are phenyl or naphthyl, notably phenyl. The aryl group may be unsubstituted or substituted as explicitly defined. The sub-group wherein aryl groups are phenyl rings fused to a 5- or 6-membered saturated or partially unsaturated non-aromatic ring optionally containing 1 or 2 oxygen atoms is preferably unsubstituted, or mono-, or di-substituted wherein the substituents are independently selected from the group consisting of methyl, methoxy, and halogen.

For the substituent $Ar^1$ particular examples of aryl groups are phenyl, 2-naphthyl, 6-methoxy-naphthalen-2-yl, 1-naphthyl, 4-chlorophenyl, 3-chlorophenyl, 2-chlorophenyl, 4-fluorophenyl, 3-fluorophenyl, 2-fluorophenyl, 4-methylphenyl, 3-methylphenyl, 2-methylphenyl, 2,6-dimethylphenyl, 3-fluoro-4-methylphenyl, 3-chloro-4-methylphenyl, 4-fluoro-3-methylphenyl, 3,4-difluorophenyl, 3-chloro-4-fluorophenyl, 4-chloro-2-fluorophenyl, 4-chloro-3-fluorophenyl, 3-chloro-6-fluorophenyl, 2-chloro-4-fluorophenyl, 3,4-dichlorophenyl, 2,4-dichlorophenyl, 2,5-dichlorophenyl, 2,6-dichlorophenyl, 3,4-difluoro-phenyl, 3,5-difluoro-phenyl, 2,5-difluoro-phenyl, 2,6-difluoro-phenyl, 3,4,5-trifluoro-phenyl, 2-chloro-3,6-difluorophenyl, 4-methoxyphenyl, 3-methoxyphenyl, 2-methoxyphenyl, 2,3-dimethoxyphenyl, 2,4-dimethoxyphenyl, 3,4-dimethoxyphenyl, 2,4,6-trimethylphenyl, 4-ethoxyphenyl, 2-ethoxyphenyl, 4-(n-propoxy)phenyl, 4-isopropoxyphenyl, 4-trifluoromethylphenyl, 3-trifluoromethylphenyl, 2-trifluoromethylphenyl, 4-tert.butyl-phenyl, 2,6-dimethoxyphenyl, 2,5-dimethoxyphenyl, 2-difluoromethoxy-phenyl, 4-difluoromethoxyphenyl, 4-trifluoromethyl-sulfanyl-phenyl, 4-trifluoromethoxyphenyl, 3-trifluoromethoxyphenyl, 2-trifluoromethoxyphenyl, 2-methyl-3-trifluoromethylphenyl, 2-methyl-5-trifluoromethylphenyl, 3-fluoro-4-trifluoromethylphenyl, 4-fluoro-3-trifluoromethylphenyl, 2-fluoro-4-trifluoromethylphenyl, 2-fluoro-5-trifluoromethylphenyl, 2-chloro-5-trifluoromethylphenyl, 4-chloro-3-trifluoromethylphenyl, 2-fluoro-3-chloro-5-trifluoromethylphenyl, 3-fluoro-4-trifluoromethoxyphenyl, 3-chloro-4-trifluoromethoxyphenyl, 4-(2,2,2-trifluoroethoxy)phenyl, 4-tert.-butoxyphenyl, 4-(cyclopropylmethoxy)-phenyl, benzo[1,3]dioxol-5-yl, 2,2-difluoro-benzo[1,3]dioxol-5-yl, 2,3-dihydrobenzofuran-5-yl, and 2,3-dihydro-benzo[1,4]dioxin-6-yl. In a sub-embodiment examples are 2-naphthyl, 4-chlorophenyl, 2-chlorophenyl, 4-fluorophenyl, 2-fluorophenyl, 3-methylphenyl, 2-methylphenyl, 2,6-dimethylphenyl, 3-chloro-4-methylphenyl, 4-fluoro-3-methylphenyl, 3,4-difluorophenyl, 3-chloro-4-fluorophenyl, 4-chloro-2-fluorophenyl, 4-chloro-3-fluorophenyl, 3,4-dichlorophenyl, 2,4-dichlorophenyl, 2,5-dichlorophenyl, 2,6-dichlorophenyl, 2-chloro-3,6-difluorophenyl, 4-methoxyphenyl, 3-methoxyphenyl, 2,4,6-trimethylphenyl, 4-ethoxyphenyl, 4-(n-propoxy)phenyl, 4-isopropoxyphenyl, 4-trifluoromethylphenyl, 3-trifluoromethylphenyl, 4-difluoromethoxyphenyl, 4-trifluoromethyl-sulfanyl-phenyl, 4-trifluoromethoxyphenyl, 3-trifluoromethoxyphenyl, 2-trifluoromethoxyphenyl, 2-methyl-3-trifluoromethylphenyl, 2-methyl-5-trifluoromethylphenyl, 3-fluoro-4-trifluoromethylphenyl, 4-fluoro-3-trifluoromethyl phenyl, 2-fluoro-4-trifluoromethyl phenyl, 2-fluoro-5-trifluoromethylphenyl, 2-chloro-5-trifluoromethylphenyl, 4-chloro-3-trifluoromethyl phenyl, 2-fluoro-3-chloro-5-trifluoromethylphenyl, 3-fluoro-4-trifluoromethoxyphenyl, 3-chloro-4-trifluoromethoxyphenyl, 4-(cyclopropylmethoxy)-phenyl, and benzo[1,3]dioxol-5-yl.

For the substituent $R^4$ particular examples of aryl groups are 2-methoxy-naphthalen-1-yl, 2,6-difluorophenyl, 2-methoxyphenyl, 2-ethoxyphenyl, 2-fluoro-6-methoxyphenyl, 2-chloro-6-methoxyphenyl, 2-methoxy-6-methylphenyl, 2-methoxy-5-methylphenyl, 2,6-dimethylphenyl, 2,6-dimethoxyphenyl, 2,5-dimethoxyphenyl, 3-chloro-2,6-dimethoxyphenyl, 2-chloro-4,6-dimethoxyphenyl, 2-fluoro-4,6-dimethoxyphenyl, 4-fluoro-2,6-dimethoxyphenyl, 2-ethoxy-6-methoxyphenyl, 2,6-diethoxyphenyl, 2-isopropoxy-6-methoxyphenyl, 3-fluoro-2,6-dimethoxyphenyl, 2,6-dimethoxy-3-methylphenyl, 2,6-dimethoxy-4-methylphenyl, 2-(2-hydroxyethoxy)-6-methoxyphenyl, 2-(2-hydroxypropoxy)-6-methoxyphenyl, 2-(3-hydroxypropoxy)-6-methoxyphenyl, 2-(2,3-dihydroxypropoxy)-6-methoxyphenyl, 2-(2-methoxyethoxy)-6-methoxyphenyl, 2,3,6-trimethoxyphenyl, 2,4,6-trimethoxyphenyl, 2-trifluoromethylphenyl, 2-methoxy-6-trifluoromethylphenyl, 6-methoxy-indan-5-yl, benzo[1,3]dioxol-4-yl, 5-methoxy-benzo[1,3]dioxol-4-yl, 5-bromo-benzo[1,3]dioxol-4-yl, 2,2-dimethyl-2,3-dihydrobenzofuran-7-yl, 2,3-dihydro-benzo[1,4]dioxin-5-yl, and 6-methoxy-2,3-dihydro-benzo[1,4]dioxin-5-yl. In a sub-embodiment, examples are 2-ethoxyphenyl, 2-fluoro-6-methoxyphenyl, 2-chloro-6-methoxyphenyl, 2-methoxy-6-methylphenyl, 2,6-dimethylphenyl, 2,6-dimethoxyphenyl, 2-ethoxy-6-methoxyphenyl, 4-fluoro-2,6-dimethoxyphenyl, 2,6-dimethoxy-4-methylphenyl, 2-(2-hydroxyethoxy)-6-methoxyphenyl, 2-methoxy-6-trifluoromethylphenyl, 5-methoxy-benzo[1,3]dioxol-4-yl, and 6-methoxy-2,3-dihydro-benzo[1,4]dioxin-5-yl. In another sub-embodiment, examples are 2-ethoxyphenyl, 2-fluoro-6-methoxyphenyl, 2-chloro-6-methoxyphenyl, 2-methoxy-6-methylphenyl, 2,6-dimethylphenyl, 2,6-dimethoxyphenyl, 2-ethoxy-6-methoxyphenyl, and 2-methoxy-6-trifluoromethylphenyl.

For the substituent $Ar^1$ examples of the particular sub-group of "phenyl rings fused to a 5- or 6-membered saturated or partially unsaturated non-aromatic ring optionally containing 1 to 2 oxygen atoms" are 2,2-difluoro-benzo[1,3]dioxol-5-yl, benzo[1,3]dioxol-5-yl, 2,3-dihydrobenzofuran-5-yl, and 2,3-dihydro-benzo[1,4]dioxin-6-yl (notably benzo[1,3]dioxol-5-yl).

For the substituent $R^4$ examples of the particular sub-group of "phenyl rings fused to a 5- or 6-membered saturated or partially unsaturated non-aromatic ring optionally containing 1 to 2 oxygen atoms" are 6-methoxy-indan-5-yl, benzo[1,3]dioxol-4-yl, 5-methoxy-benzo[1,3]dioxol-4-yl, 5-bromo-benzo[1,3]dioxol-4-yl, 2,2-dimethyl-2,3-dihydrobenzofuran-7-yl, 2,3-dihydro-benzo[1,4]dioxin-5-yl, and 6-methoxy-2,3-dihydro-benzo[1,4]dioxin-5-yl (notably 5-methoxy-benzo[1,3]dioxol-4-yl, and 6-methoxy-2,3-dihydro-benzo[1,4]dioxin-5-yl).

For the substituent $R^4$ examples of the particular sub-group of "bicyclic aryl" are naphthyl, indanyl, tetrahydronaphthyl, benzo[1,3]dioxolyl, 2,3-dihydrobenzofuranyl, 2,3-dihydro-benzo[1,4]dioxinyl, chromanyl, and chromenyl (notably naphthyl, benzo[1,3]dioxolyl, and 2,3-dihydro-benzo[1,4]dioxinyl) which are unsubstituted or substituted as explicitly defined. Particular examples are 2-methoxy-naphthalen-1-yl, 5-methoxy-benzo[1,3]dioxol-4-yl, and 6-methoxy-2,3-dihydro-benzo[1,4]dioxin-5-yl.

The term "heteroaryl", alone or in combination, means a 5- to 10-membered monocyclic or bicyclic aromatic ring containing 1 to a maximum of 3 heteroatoms independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, 4H-furo[3,2-b]pyrrolyl, pyrrolo[2,1-b]thiazolyl and imidazo[2,1-b]thiazolyl. In case the heteroaryl group is a 5- to 6-membered heteroaryl as used for the generic groups $Ar^2$ and $Ar^3$, particular examples are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, and pyrazinyl; notably pyrrolyl, pyrazolyl, pyridyl, pyrimidyl, pyridazinyl, and pyrazinyl. The heteroaryl group may be unsubstituted or substituted as explicitly defined.

For the substituent $Ar^1$ particular examples of heteroaryl groups are thiophenyl, pyrrolyl, pyridazinyl, pyridinyl, benzo[b]thiophenyl, benzofuranyl, benzimidazolyl, benzoxazolyl, benzothiazolyl, indolyl, benzotriazolyl, quinoxalinyl, and quinolinyl, which are unsubstituted or substituted as explicitly defined; notably thiophen-2-yl, 1-methyl-pyrrol-2-yl, 6-ethoxy-pyridazin-3-yl, pyridin-2-yl, pyridin-4-yl, 2-ethoxy-pyridin-5-yl, 5-ethoxy-pyridin-2-yl, benzo[b]thiophen-2-yl, benzo[b]thiophen-3-yl, benzo[b]thiophen-5-yl, benzofuran-2-yl, 1H-benzimidazol-2-yl, 1-methyl-1H-benzimidazol-2-yl, benzoxazol-2-yl, benzothiazol-2-yl, 1-methyl-1H-indol-6-yl, 1H-indol-2-yl, 1-methyl-1H-indol-2-yl, 1H-indol-3-yl, 1-methyl-1H-benzotriazol-5-yl, quinoxalin-2-yl, quinoxalin-6-yl, quinolin-2-yl, quinolin-6-yl, and quinolin-7-yl (especially benzimidazol-2-yl, benzoxazol-2-yl, and benzothiazol-2-yl).

For the substituent $R^4$ particular examples of heteroaryl groups are pyridinyl, benzo[d]isoxazolyl, benzoxazolyl, and quinolinyl which are unsubstituted or substituted as explicitly defined; notably 2,4-dimethoxypyridin-3-yl, 3,5-dimethoxypyridin-4-yl, 6-methoxy-3-methyl-benzo[d]isoxazol-7-yl, 6-methoxy-2-methyl-benzoxazol-7-yl, and 7-methoxy-quinolin-8-yl.

For the substituent $R^4$ examples of the particular sub-group of "bicyclic heteroaryl" are benzo[d]isoxazolyl, benzoxazolyl, and quinolinyl which are unsubstituted or substituted as explicitly defined. Particular examples are 6-methoxy-3-methyl-benzo[d]isoxazol-7-yl, 6-methoxy-2-methyl-benzoxazol-7-yl, and 7-methoxy-quinolin-8-yl.

For the substituent $Ar^3$ examples of the particular sub-group of "5- to 6-membered heteroaryl" are pyrrolyl, pyrazolyl, thiazolyl, oxazolyl, pyridinyl, pyrimidinyl, pyridazinyl, and pyrazinyl which are unsubstituted or substituted as explicitly defined; notably pyrrol-1-yl, pyrazol-1-yl, thiazol-2-yl, pyridin-2-yl, pyridin-3-yl, 3-methyl-pyridin-2-yl, 4-methyl-pyridin-2-yl, 5-methyl-pyridin-2-yl, 6-methyl-pyridin-2-yl, 5-methoxy-pyridin-2-yl, 6-methoxy-pyridin-2-yl, 6-trifluoromethyl-pyridin-2-yl, pyrimidin-2-yl, pyrimidin-5-yl, 6-methyl-pyridazin-3-yl, and pyrazin-2-yl. Preferred (for the substituent $Ar^3$, and mutatis mutandis also for the substituent $R^{15}$) are thiazolyl, pyridyl and pyrazinyl which are unsubstituted or substituted as explicitly defined; notably thiazol-2-yl, pyridin-2-yl, pyridin-3-yl, 4-methyl-pyridin-2-yl, and pyrazin-2-yl; especially thiazol-2-yl, and pyridin-2-yl.

For the substituent $Ar^2$ the phenyl or 5- to 6-membered heteroaryl are preferably substituted by Z and the rest of the molecule in a para (such as phenyl-1,4-diyl) arrangement (for phenyl or 6-membered heteroaryl) or in a 1,3-arrangement (for 5-membered heteroaryl). A particular example of $Ar^2$ representing a 5- to 6-membered heteroaryl group is pyridyl, notably pyridin-2,5-diyl (wherein Z may be attached in either position 2 or 5).

The term "fluoroalkyl-thio" refers to an alkyl group as defined before containing one to three carbon atoms in which one or more (and possibly all) hydrogen atoms have been replaced with fluorine, said group being attached to the rest of the molecule via a sulfur atom. The term "$(C_{x-y})$fluoroalkyl-thio" (x and y each being an integer) refers to a fluoroalkyl-thio group as defined before containing x to y carbon atoms. For example a $(C_{1-3})$fluoroalkyl-thio group contains from one to three carbon atoms in which one to seven hydrogen atoms have been replaced with fluorine. A representative example of a fluoroalkyl-thio group is trifluoromethyl-sulfanyl ($F_3C$—S—).

The term "$(C_{3-6})$cycloalkyl-$(C_{1-4})$alkoxy" refers to a $(C_{1-4})$alkoxy group as defined before containing one to four carbon atoms in which one hydrogen atom has been replaced with a $(C_{3-6})$cycloalkyl group as defined before. A representative example of $(C_{3-6})$cycloalkyl-$(C_{1-4})$alkoxy groups is cyclopropylmethoxy.

The term "hydroxy-$(C_{1-4})$alkoxy" refers to an alkoxy group as defined before containing one to four carbon atoms in which one hydrogen atom has been replaced with hydroxy. Representative examples of hydroxy-$(C_{1-4})$alkoxy groups are 2-hydroxy-ethoxy and 2-hydroxy-propoxy (notably 2-hydroxy-ethoxy).

The term "dihydroxy-$(C_{1-4})$alkoxy" refers to refers to an alkoxy group as defined before containing one to four carbon atoms in which two hydrogen atoms have been replaced with hydroxy. A representative example of a dihydroxy-$(C_{1-4})$alkoxy group is 2,3-dihydroxy-propoxy.

The term "$(C_{1-4})$alkoxy-$(C_{1-4})$alkoxy" refers to an alkoxy group as defined before containing one to four carbon atoms in which one hydrogen atom has been replaced with a $(C_{1-4})$alkoxy group as defined before. A representative example of a $(C_{1-4})$alkoxy-$(C_{1-4})$alkoxy group is 2-methoxy-ethoxy.

Further embodiments of the invention are presented hereafter:

2) A further embodiment of the invention relates to compounds according to embodiment 1), which are also compounds of formula ($I_{E1}$) wherein the stereocenter at position 2 of the oxazolidinone moiety is in absolute (S)-configuration:

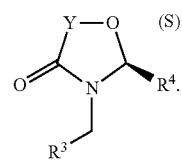

Formula ($I_{E1}$)

3) A further embodiment of the invention relates to compounds according to embodiment 1), which are also compounds of formula ($I_{E2}$) wherein the stereocenter at position 2 of the oxazolidinone moiety is in absolute (R)-configuration:

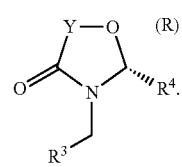

Formula ($I_{E2}$)

4) A further embodiment of the invention relates to compounds according to any one of embodiments 1) to 5), wherein Y represents $CHR^1$, or $CR^1R^2$; wherein each group forms a particular sub-embodiment.

5) A further embodiment of the invention relates to compounds according to any one of embodiments 1) to 5), wherein Y represents $CH_2$.

6) A further embodiment of the invention relates to compounds according to any one of embodiments 1) to 4), wherein, if present, $R^1$ represents methyl and, if present, $R^2$ represents methyl.

7) A further embodiment of the invention relates to compounds according to any one of embodiments 1) to 6), wherein $R^3$ represents $Ar^1$.

8) A further embodiment of the invention relates to compounds according to any one of embodiments 1) to 6), wherein $R^3$ represents $Ar^3$—Z—$Ar^2$—* wherein the asterisk indicates the bond that is attached to the rest of the molecule.

9) A further embodiment of the invention relates to compounds according to any one of embodiments 1) to 7), wherein
   $Ar^1$ represents aryl which is unsubstituted, or mono-, di-, or tri-substituted (notably mono-, or di-substituted), wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, $(C_{1-3})$fluoroalkyl-thio-, and $(C_{3-6})$cycloalkyl-$(C_{1-4})$alkoxy (notably $(C_{1-4})$alkyl, $(C_{1-4})$alkoxy, halogen, $(C_{1-3})$fluoroalkyl, and $(C_{1-3})$fluoroalkoxy); or
   $Ar^1$ represents heteroaryl which is unsubstituted, or mono-, di-, or tri-substituted (notably mono-, or di-substituted), wherein the substituents are independently selected from the group consisting of $(C_{1-4})$alkyl, $(C_{1-4})$alkoxy and $(C_{1-3})$fluoroalkyl (notably $(C_{1-4})$alkyl).

10) A further embodiment of the invention relates to compounds according to any one of embodiments 1) to 7), wherein
    $Ar^1$ represents aryl which is unsubstituted, or mono-, di-, or tri-substituted (notably mono-, or di-substituted), wherein the substituents are independently selected from the group consisting of $(C_{1-4})$alkyl, $(C_{1-4})$alkoxy, halogen, $(C_{3-6})$cycloalkyl-$(C_{1-4})$alkoxy, $(C_{1-3})$fluoroalkyl, and (C$_{1-3}$)fluoroalkoxy (notably (C$_{1-4}$)alkyl, (C$_{1-4}$)alkoxy, halogen, (C$_{1-3}$)fluoroalkyl, and (C$_{1-3}$)fluoroalkoxy).

11) A further embodiment of the invention relates to compounds according to any one of embodiments 1) to 7), 9) or 10), wherein, in case Ar$^1$ represents aryl, said aryl is
   phenyl which is unsubstituted, or mono-, di-, or tri-substituted (notably mono-, or di-substituted), wherein the substituents are independently selected from the group consisting of (C$_{1-4}$)alkyl, (C$_{1-4}$)alkoxy, halogen, (C$_{1-3}$)fluoroalkyl, (C$_{1-3}$)fluoroalkoxy, (C$_{1-3}$)fluoroalkyl-thio-, and (C$_{3-6}$)cycloalkyl-(C$_{1-4}$)alkoxy (notably (C$_{1-4}$)alkyl, (C$_{1-4}$)alkoxy, halogen, (C$_{1-3}$)fluoroalkyl, and (C$_{1-3}$)fluoroalkoxy); or
   naphthyl (notably 2-naphthyl) which is unsubstituted, or mono-, or di-substituted (notably unsubstituted or mono-substituted), wherein the substituents are independently selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably (C$_{1-4}$)alkoxy); or
   a phenyl ring fused to a 5- or 6-membered saturated or partially unsaturated non-aromatic ring optionally containing 1 to 2 oxygen atoms (notably an indanyl, a benzo[1,3]dioxolyl, a 2,3-dihydrobenzofuranyl, or a 2,3-dihydro-benzo[1,4]dioxinyl group) which is (preferably) unsubstituted, or mono-, or di-substituted wherein the substituents are independently selected from the group consisting of methyl, methoxy, and halogen.

12) A further embodiment of the invention relates to compounds according to any one of embodiments 1) to 7), wherein
   Ar$^1$ represents heteroaryl which is unsubstituted, or mono-, or di-substituted, wherein the substituents are independently selected from the group consisting of (C$_{1-4}$)alkyl, (C$_{1-4}$)alkoxy and (C$_{1-3}$)fluoroalkyl (notably (C$_{1-4}$)alkyl).

13) A further embodiment of the invention relates to compounds according to any one of embodiments 1) to 6), 8) or 11), wherein Ar$^2$ represents phenyl (notably phenyl-1,4-diyl).

14) A further embodiment of the invention relates to compounds according to any one of embodiments 1) to 6), 8) or 11), wherein Ar$^2$ represents 5- to 6-membered heteroaryl (notably 6-membered heteroaryl).

15) A further embodiment of the invention relates to compounds according to any one of embodiments 1) to 6), 8), 11), 13) or 14), wherein Z represents a O.

16) A further embodiment of the invention relates to compounds according to any one of embodiments 1) to 6), 8), 11), 13) or 14), wherein Z represents a bond.

17) A further embodiment of the invention relates to compounds according to any one of embodiments 1) to 6), 8), 11), or 13) to 16), wherein
   Ar$^3$ represents phenyl which is unsubstituted, or mono-, di-, or tri-substituted (notably unsubstituted or mono-substituted), wherein the substituents are independently selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably Ar$^3$ represents unsubstituted phenyl); or
   Ar$^3$ represents 5- to 6-membered heteroaryl which is unsubstituted, or mono-, di-, or tri-substituted (notably unsubstituted or mono-substituted), wherein the substituents are independently selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably substituents are selected from (C$_{1-4}$)alkyl, (C$_{1-4}$)alkoxy, and (C$_{1-3}$)fluoroalkyl).

18) A further embodiment of the invention relates to compounds according to any one of embodiments 1) to 6), 8), 11), or 13) to 16), wherein
   Ar$^3$ represents 5- to 6-membered heteroaryl which is unsubstituted, or mono-, di-, or tri-substituted (notably unsubstituted or mono-substituted), wherein the substituents are independently selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably substituents are selected from (C$_{1-4}$)alkyl, (C$_{1-4}$)alkoxy, and (C$_{1-3}$)fluoroalkyl).

19) A further embodiment of the invention relates to compounds according to any one of embodiments 1) to 6), 8), 11), or 13) to 16), wherein
   Ar$^3$ represents phenyl which is unsubstituted, or mono-, di-, or tri-substituted, (notably unsubstituted or mono-substituted) wherein the substituents are independently selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably Ar$^3$ represents unsubstituted phenyl).

20) A further embodiment of the invention relates to compounds according to any one of embodiments 1) to 6), wherein R$^3$ represents
   phenyl which is mono-, or di-substituted, wherein one substituent is (C$_{1-4}$)alkyl, or (C$_{1-3}$)fluoroalkyl in position 4 of said phenyl and the other (if present) is selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably halogen); or
   Ar$^3$—Z—Ar$^2$—* wherein the asterisk indicates the bond that is attached to the rest of the molecule; wherein
      Ar$^2$ represents phenyl or 6-membered heteroaryl which are substituted by Z and the rest of the molecule in a para arrangement,
      Z represents O, and
      Ar$^3$ represents phenyl or 5- to 6-membered heteroaryl wherein the phenyl or 5- to 6-membered heteroaryl is independently unsubstituted or mono-substituted, wherein the substituent is independently selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably Ar$^3$ represents unsubstituted phenyl or 5- to 6-membered heteroaryl).

21) A further embodiment of the invention relates to compounds according to any one of embodiments 1) to 20), wherein
   R$^4$ represents aryl which is mono-, di-, or tri-substituted (notably mono-, or di-substituted), wherein the substituents are independently selected from the group consisting of (C$_{1-4}$)alkyl, (C$_{1-4}$)alkoxy, halogen, (C$_{1-3}$)fluoroalkyl, (C$_{1-3}$)fluoroalkoxy, hydroxy-(C$_{1-4}$)alkoxy, and (C$_{1-4}$)alkoxy-(C$_{1-4}$)alkoxy (notably substituents are selected from (C$_{1-4}$)alkyl, (C$_{1-4}$)alkoxy, halogen, (C$_{1-3}$)fluoroalkyl, (C$_{1-3}$)fluoroalkoxy, and hydroxy-(C$_{1-4}$)alkoxy); wherein, in the specific case wherein said aryl is a bicyclic ring, the aryl may also be unsubstituted; or
   R$^4$ represents heteroaryl which is mono-, di-, or tri-substituted (notably mono-, or di-substituted), wherein the substituents are independently selected from the group consisting of (C$_{1-4}$)alkyl, (C$_{1-4}$)alkoxy, halogen, (C$_{1-3}$)fluoroalkyl, (C$_{1-3}$)fluoroalkoxy, hydroxy-(C$_{1-4}$)alkoxy, and (C$_{1-4}$)alkoxy-(C$_{1-4}$)alkoxy; (notably substituents are selected from (C$_{1-4}$)alkyl, and (C$_{1-4}$)alkoxy) wherein, in the specific case wherein said heteroaryl is a bicyclic ring, the heteroaryl may also be unsubstituted.

22) A further embodiment of the invention relates to compounds according to any one of embodiments 1) to 21), wherein
R⁴ represents aryl which is mono-, di-, or tri-substituted (notably mono-, or di-substituted), wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, hydroxy-$(C_{1-4})$alkoxy, and $(C_{1-4})$alkoxy-$(C_{1-4})$alkoxy (notably substituents are selected from $(C_{1-4})$alkyl, $(C_{1-4})$alkoxy, halogen, $(C_{1-3})$ fluoroalkyl, $(C_{1-3})$fluoroalkoxy, and hydroxy-$(C_{1-4})$ alkoxy); wherein, in the specific case wherein said aryl is a bicyclic ring, the aryl may also be unsubstituted.

23) A further embodiment of the invention relates to compounds according to any one of embodiments 1) to 21), wherein
R⁴ represents heteroaryl which is mono-, di-, or tri-substituted (notably mono-, or di-substituted), wherein the substituents are independently selected from the group consisting of $(C_{1-4})$alkyl, $(C_{1-4})$alkoxy, halogen, $(C_{1-3})$ fluoroalkyl, $(C_{1-3})$fluoroalkoxy, hydroxy-$(C_{1-4})$alkoxy, and $(C_{1-4})$alkoxy-$(C_{1-4})$alkoxy; (notably substituents are selected from $(C_{1-4})$alkyl, and $(C_{1-4})$alkoxy) wherein, in the specific case wherein said heteroaryl is a bicyclic ring, the heteroaryl may also be unsubstituted.

24) A further embodiment of the invention relates to compounds according to any one of embodiments 1) to 22), wherein, in case R⁴ represents aryl, said aryl is
phenyl which is mono-, di-, or tri-substituted (notably mono-, or di-substituted), wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, hydroxy-$(C_{1-4})$alkoxy, and $(C_{1-4})$ alkoxy-$(C_{1-4})$alkoxy (notably substituents are selected from $(C_{1-4})$alkyl, $(C_{1-4})$alkoxy, halogen, $(C_{1-3})$fluoroalkyl, $(C_{1-3})$fluoroalkoxy, and hydroxy-$(C_{1-4})$alkoxy); or
naphthyl (notably 1-naphthyl) which is unsubstituted, or mono-, or di-substituted (notably mono-substituted), wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy (notably $(C_{1-4})$alkoxy); or
a phenyl ring fused to a 5- or 6-membered saturated or partially unsaturated non-aromatic ring optionally containing 1 to 2 oxygen atoms (notably a 2,3-dihydrobenzo[1,4]dioxinyl group) which is unsubstituted, or mono-, or di-substituted (notably mono-substituted) wherein the substituents are independently selected from the group consisting of methyl, methoxy, and halogen (notably methoxy).

25) A further embodiment of the invention relates to compounds according to any one of embodiments 1) to 24), wherein R⁴ is at least mono-substituted, wherein said substituent is attached in ortho position to the point of attachment of R⁴ to the rest of the molecule; wherein, in case R⁴ represents a phenyl group, said substituent is preferably selected from the group consisting of $(C_{1-4})$alkoxy, $(C_{1-3})$ fluoroalkoxy, and hydroxy-$(C_{1-4})$alkoxy (notably $(C_{1-4})$ alkoxy); and, in case R⁴ represents a group different from phenyl, said substituent is preferably methoxy.

26) Another embodiment relates to compounds of formula (I) according to embodiment 1) which are also compounds of formula (II):

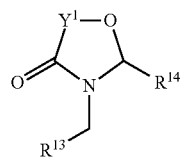

Formula (II)

wherein
Y¹ represents CH₂, CH(CH₃) or CH(CH₃)₂;
R¹³ represents

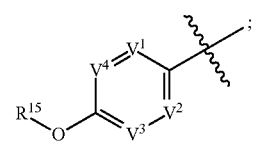

wherein
R¹⁵ represents $(C_{1-4})$alkyl or $(C_{1-3})$fluoroalkyl;
V¹, V² and V⁴ are CH, and V³ is CR¹⁷, wherein optionally one or two of V¹, V², V³ and V⁴ may also be N; and
R¹⁷ is hydrogen or halogen; or
R¹⁵ represents phenyl or 5- to 6-membered heteroaryl, wherein the phenyl or 5- to 6-membered heteroaryl is independently unsubstituted, or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy (notably R¹⁵ represents unsubstituted phenyl or 5- to 6-membered heteroaryl); and one or two of V¹, V², V³ and V⁴ are CH or N and the remaining are CH; and
R¹⁴ represents a group selected from the group consisting of:

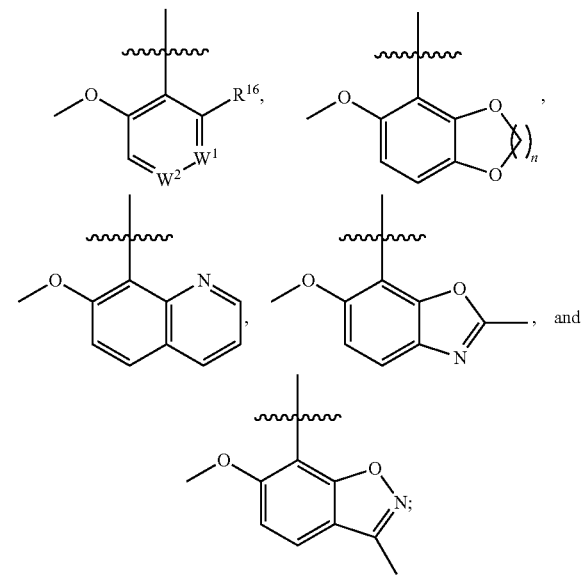

wherein
W¹ represents CH and W² represents CR¹⁷ or N, or W¹ represents N and W² represents CH;
R¹⁶ represents methyl, $(C_{1-3})$alkoxy, halogen, $(C_{1-2})$fluoroalkoxy, or trifluoromethyl (notably methyl, methoxy, ethoxy, fluoro, chloro, or trifluoromethyl);

R$^{17}$ represents hydrogen, methyl or fluoro (notably hydrogen); and n represents the integer 1 or 2;

wherein characteristics described for compounds of formula (I), notably those described in embodiments 2) to 5), apply mutatis mutandis also to compounds of formula (II).

27) A further embodiment of the invention relates to compounds of formula (II) according to embodiments 26); wherein, R$^{15}$ represents (C$_{1-4}$)alkyl; (C$_{1-3}$)fluoroalkyl;

V$^1$, V$^2$ and V$^4$ are CH, and V$^3$ is CR$^{18}$, wherein optionally one or two of V$^1$, V$^2$, V$^3$ and V$^4$ may also be N; and R$^{18}$ is hydrogen or halogen.

28) A further embodiment of the invention relates to compounds of formula (II) according to embodiments 26) or 27); wherein, R$^{15}$ represents phenyl or 5- to 6-membered heteroaryl, wherein the phenyl or 5- to 6-membered heteroaryl is independently unsubstituted, or mono-substituted, wherein the substituent is selected from the group consisting of (C$_{1-4}$)alkyl, (C$_{1-4}$)alkoxy, halogen, (C$_{1-3}$)fluoroalkyl, and (C$_{1-3}$)fluoroalkoxy (notably R$^{15}$ represents unsubstituted phenyl or 5- to 6-membered heteroaryl); and one or two of V$^1$, V$^2$, V$^3$ and V$^4$ are CH or N and the remaining are CH.

29) A further embodiment of the invention relates to compounds of formula (II) according to any one of embodiments 26) to 28); wherein, R$^{14}$ represents

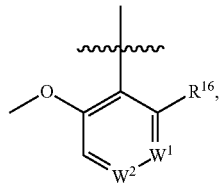

wherein

W$^1$ represents CH and W$^2$ represents CR$^{17}$ or N; or
W$^1$ represents N and W$^2$ represents CH;

R$^{16}$ represents methyl, (C$_{1-3}$)alkoxy, halogen, (C$_{1-2}$)fluoroalkoxy, or trifluoromethyl (notably methoxy or ethoxy);

R$^{17}$ represents hydrogen, methyl or fluoro (notably hydrogen);

wherein each combination of W$^1$, W$^2$, R$^{16}$ and R$^{17}$ constitutes a particular sub-embodiment.

30) A further embodiment of the invention relates to compounds of formula (II) according to embodiment 29); wherein W$^1$ represents CH; W$^2$ represents CR$^{17}$; R$^{16}$ represents methoxy; and R$^{17}$ represents hydrogen, or fluoro (notably hydrogen);

31) A further embodiment of the invention relates to compounds of formula (II) according to any one of embodiments 26) to 30); wherein, Y$^1$ represents CH$_2$.

32) A further embodiment of the invention relates to compounds of formula (II) according to any one of embodiments 26) to 30); wherein, Y$^1$ represents CH(CH$_3$).

33) A further embodiment of the invention relates to compounds of formula (II) according to any one of embodiments 26) to 30); wherein, Y$^1$ represents CH(CH$_3$)$_2$.

The compounds of formula (I) may contain one or more stereogenic or asymmetric centers, such as one or more asymmetric carbon atoms. The compounds of formulae (I) and (II) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to compounds of formulae (I) or (II) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

34) Another embodiment relates to compounds of formula (I) according to embodiment 1) selected from the group consisting of:

3-(4-Chloro-3-trifluoromethyl-benzyl)-2-(2-ethoxy-phenyl)-oxazolidin-4-one;

2-(2-Ethoxy-phenyl)-3-(2-methyl-benzyl)-oxazolidin-4-one;

2-(2-Ethoxy-phenyl)-3-(4-trifluoromethyl-benzyl)-oxazolidin-4-one;

2-(2-Ethoxy-phenyl)-3-(3-methoxy-benzyl)-oxazolidin-4-one;

2-(2-Ethoxy-phenyl)-3-(3-trifluoromethyl-benzyl)-oxazolidin-4-one;

2-(2-Ethoxy-phenyl)-3-(4-trifluoromethoxy-benzyl)-oxazolidin-4-one;

2-(2-Ethoxy-phenyl)-3-(3-trifluoromethoxy-benzyl)-oxazolidin-4-one;

2-(2-Ethoxy-phenyl)-3-(4-fluoro-3-methyl-benzyl)-oxazolidin-4-one;

3-(3-Chloro-4-fluoro-benzyl)-2-(2-ethoxy-phenyl)-oxazolidin-4-one;

3-(3-Chloro-2-fluoro-5-trifluoromethyl-benzyl)-2-(2-ethoxy-phenyl)-oxazolidin-4-one;

2-(2-Ethoxy-phenyl)-3-(2-methyl-3-trifluoromethyl-benzyl)-oxazolidin-4-one;

3-(2-Chloro-5-trifluoromethyl-benzyl)-2-(2-ethoxy-phenyl)-oxazolidin-4-one;

2-(2-Ethoxy-phenyl)-3-(2-fluoro-5-trifluoromethyl-benzyl)-oxazolidin-4-one;

2-(2-Ethoxy-phenyl)-3-(4-fluoro-3-trifluoromethyl-benzyl)-oxazolidin-4-one;

2-(2-Ethoxy-phenyl)-3-(3-fluoro-4-trifluoromethyl-benzyl)-oxazolidin-4-one;

3-(2-Chloro-3,6-difluoro-benzyl)-2-(2-ethoxy-phenyl)-oxazolidin-4-one;

3-(4-Chloro-3-fluoro-benzyl)-2-(2-ethoxy-phenyl)-oxazolidin-4-one;

3-(3-Chloro-4-trifluoromethoxy-benzyl)-2-(2-ethoxy-phenyl)-oxazolidin-4-one;

3-(4-Chloro-2-fluoro-benzyl)-2-(2-ethoxy-phenyl)-oxazolidin-4-one;

2-(2-Ethoxy-phenyl)-3-(2-fluoro-benzyl)-oxazolidin-4-one;

3-(4-Chloro-benzyl)-2-(2-ethoxy-phenyl)-oxazolidin-4-one;

2-(2-Ethoxy-phenyl)-3-(2-fluoro-4-trifluoromethyl-benzyl)-oxazolidin-4-one;

3-(2,6-Dichloro-benzyl)-2-(2-ethoxy-phenyl)-oxazolidin-4-one;

2-(2-Ethoxy-phenyl)-3-(3-methyl-benzyl)-oxazolidin-4-one;

2-(2-Ethoxy-phenyl)-3-(4-fluoro-benzyl)-oxazolidin-4-one;

3-(3,4-Difluoro-benzyl)-2-(2-ethoxy-phenyl)-oxazolidin-4-one;

2-(2-Ethoxy-phenyl)-3-(4-methoxy-benzyl)-oxazolidin-4-one;
2-(2-Ethoxy-phenyl)-3-(2-methyl-5-trifluoromethyl-benzyl)-oxazolidin-4-one;
3-(3,4-Dichloro-benzyl)-2-(2-ethoxy-phenyl)-oxazolidin-4-one;
3-(2,4-Dichloro-benzyl)-2-(2-ethoxy-phenyl)-oxazolidin-4-one;
3-(3-Chloro-4-methyl-benzyl)-2-(2-ethoxy-phenyl)-oxazolidin-4-one;
2-(2,6-Dimethoxy-phenyl)-3-(4-trifluoromethyl-benzyl)-oxazolidin-4-one;
2-(2,6-Dimethoxy-phenyl)-3-(2-trifluoromethoxy-benzyl)-oxazolidin-4-one;
2-(2,6-Dimethoxy-phenyl)-3-(4-trifluoromethoxy-benzyl)-oxazolidin-4-one;
2-(2,6-Dimethoxy-phenyl)-3-(3-trifluoromethoxy-benzyl)-oxazolidin-4-one;
3-(3-Chloro-4-fluoro-benzyl)-2-(2,6-dimethoxy-phenyl)-oxazolidin-4-one;
3-(3-Chloro-2-fluoro-5-trifluoromethyl-benzyl)-2-(2,6-dimethoxy-phenyl)-oxazolidin-4-one;
2-(2,6-Dimethoxy-phenyl)-3-(4-fluoro-3-trifluoromethyl-benzyl)-oxazolidin-4-one;
3-(4-Chloro-3-fluoro-benzyl)-2-(2,6-dimethoxy-phenyl)-oxazolidin-4-one;
3-(3-Chloro-4-trifluoromethoxy-benzyl)-2-(2,6-dimethoxy-phenyl)-oxazolidin-4-one;
2-(2,6-Dimethoxy-phenyl)-3-(2,4,6-trimethyl-benzyl)-oxazolidin-4-one;
3-(2,4-Dichloro-benzyl)-2-(2,6-dimethoxy-phenyl)-oxazolidin-4-one;
3-(3-Chloro-4-methyl-benzyl)-2-(2,6-dimethoxy-phenyl)-oxazolidin-4-one;
2-(2,6-Dimethoxy-phenyl)-3-(2,6-dimethyl-benzyl)-oxazolidin-4-one;
3-(2-Chloro-benzyl)-2-(2-ethoxy-phenyl)-oxazolidin-4-one;
3-(2,5-Dichloro-benzyl)-2-(2-ethoxy-phenyl)-oxazolidin-4-one;
2-(2,6-Dimethoxy-phenyl)-3-(4-phenoxy-benzyl)-oxazolidin-4-one;
2-(2,6-Dimethoxy-phenyl)-3-(3-fluoro-4-trifluoromethoxy-benzyl)-oxazolidin-4-one;
3-(4-Difluoromethoxy-benzyl)-2-(2,6-dimethoxy-phenyl)-oxazolidin-4-one;
2-(2,6-Dimethoxy-phenyl)-5,5-dimethyl-3-(4-phenoxy-benzyl)-oxazolidin-4-one;
2-(2,6-Dimethoxy-phenyl)-(R)-5-methyl-3-(4-phenoxy-benzyl)-oxazolidin-4-one;
3-(4-Difluoromethoxy-benzyl)-2-(2,6-dimethoxy-phenyl)-(R)-5-methyl-oxazolidin-4-one;
2-(2,6-Dimethoxy-phenyl)-(R)-5-methyl-3-naphthalen-2-ylmethyl-oxazolidin-4-one;
2-(2,6-Dimethoxy-phenyl)-3-(4-propoxy-benzyl)-oxazolidin-4-one;
2-(2,6-Dimethoxy-phenyl)-3-(3-fluoro-4-trifluoromethoxy-benzyl)-(R)-5-methyl-oxazolidin-4-one;
3-(3-Chloro-4-trifluoromethoxy-benzyl)-2-(2,6-dimethoxy-phenyl)-(R)-5-methyl-oxazolidin-4-one;
2-(2,6-Dimethoxy-phenyl)-5,5-dimethyl-3-naphthalen-2-ylmethyl-oxazolidin-4-one;
3-(3-Chloro-4-trifluoromethoxy-benzyl)-2-(2,6-dimethoxy-phenyl)-5,5-dimethyl-oxazolidin-4-one;
2-(2,6-Dimethoxy-phenyl)-(S)-5-methyl-3-(4-phenoxy-benzyl)-oxazolidin-4-one;
2-(2,6-Dimethoxy-phenyl)-3-(4-isopropoxy-benzyl)-oxazolidin-4-one;
2-(2,6-Dimethoxy-phenyl)-5,5-dimethyl-3-(4-trifluoromethoxy-benzyl)-oxazolidin-4-one;
3-Benzothiazol-2-ylmethyl-2-(2,6-dimethoxy-phenyl)-(R)-5-methyl-oxazolidin-4-one;
2-(2,6-Dimethoxy-phenyl)-(R)-5-methyl-3-(4-trifluoromethoxy-benzyl)-oxazolidin-4-one;
3-Benzothiazol-2-ylmethyl-2-(2,6-dimethoxy-phenyl)-5,5-dimethyl-oxazolidin-4-one;
3-(4-Cyclopropylmethoxy-benzyl)-2-(2,6-dimethoxy-phenyl)-oxazolidin-4-one;
2-(2,6-Dimethoxy-phenyl)-(S)-5-methyl-3-naphthalen-2-ylmethyl-oxazolidin-4-one;
2-(2,6-Dimethoxy-phenyl)-3-(3-fluoro-4-trifluoromethoxy-benzyl)-5,5-dimethyl-oxazolidin-4-one;
3-Benzooxazol-2-ylmethyl-2-(2,6-dimethoxy-phenyl)-5,5-dimethyl-oxazolidin-4-one;
3-(4-Difluoromethoxy-benzyl)-2-(2,6-dimethoxy-phenyl)-5,5-dimethyl-oxazolidin-4-one;
2-(2,6-Dimethoxy-phenyl)-5,5-dimethyl-3-(1-methyl-1H-benzoimidazol-2-ylmethyl)-oxazolidin-4-one;
3-Benzo[1,3]dioxol-5-ylmethyl-2-(2,6-dimethoxy-phenyl)-5,5-dimethyl-oxazolidin-4-one;
2-(2,6-Dimethoxy-phenyl)-3-(4-methoxy-benzyl)-5,5-dimethyl-oxazolidin-4-one;
(R)-2-(2,6-Dimethoxy-phenyl)-5-methyl-3-(4-propoxy-benzyl)-oxazolidin-4-one;
2-(2,6-Dimethoxy-phenyl)-3-(4-isopropoxy-benzyl)-(R)-5-methyl-oxazolidin-4-one;
3-(4-Cyclopropylmethoxy-benzyl)-2-(2,6-dimethoxy-phenyl)-(R)-5-methyl-oxazolidin-4-one;
2-(2,6-Dimethoxy-phenyl)-3-(4-isopropoxy-benzyl)-5,5-dimethyl-oxazolidin-4-one;
2-(2,6-Dimethoxy-phenyl)-5,5-dimethyl-3-(4-propoxy-benzyl)-oxazolidin-4-one;
3-(4-Cyclopropylmethoxy-benzyl)-2-(2,6-dimethoxy-phenyl)-5,5-dimethyl-oxazolidin-4-one;
2-(2,6-Dimethoxy-phenyl)-3-(4-ethoxy-benzyl)-(R)-5-methyl-oxazolidin-4-one;
2-(2,6-Dimethoxy-phenyl)-3-(4-ethoxy-benzyl)-5,5-dimethyl-oxazolidin-4-one;
3-(3-Chloro-4-trifluoromethoxy-benzyl)-2-(2,6-dimethyl-phenyl)-5,5-dimethyl-oxazolidin-4-one;
3-(3-Chloro-4-trifluoromethoxy-benzyl)-2-(2,6-difluoro-phenyl)-5,5-dimethyl-oxazolidin-4-one;
3-(3-Chloro-4-trifluoromethoxy-benzyl)-2-(2-methoxy-6-methyl-phenyl)-5,5-dimethyl-oxazolidin-4-one;
2-(2-Fluoro-6-methoxy-phenyl)-5,5-dimethyl-3-(4-phenoxy-benzyl)-oxazolidin-4-one;
2-(2-Chloro-6-methoxy-phenyl)-5,5-dimethyl-3-(4-phenoxy-benzyl)-oxazolidin-4-one;
2-(2-Methoxy-6-trifluoromethyl-phenyl)-5,5-dimethyl-3-(4-phenoxy-benzyl)-oxazolidin-4-one;
3-Biphenyl-4-ylmethyl-2-(2,6-dimethoxy-phenyl)-5,5-dimethyl-oxazolidin-4-one;
2-(2,6-Dimethoxy-phenyl)-5,5-dimethyl-3-(4-trifluoromethylsulfanyl-benzyl)-oxazolidin-4-one;
2-(2,6-Dimethoxy-phenyl)-5,5-dimethyl-3-(6-phenoxy-pyridin-3-ylmethyl)-oxazolidin-4-one;
2-(2,6-Dimethoxy-phenyl)-5,5-dimethyl-3-(5-phenoxy-pyridin-2-ylmethyl)-oxazolidin-4-one;
2-(2,6-Dimethoxy-phenyl)-5,5-dimethyl-3-[4-(pyridin-2-yloxy)-benzyl]-oxazolidin-4-one;
2-(2,6-Dimethoxy-phenyl)-5,5-dimethyl-3-[4-(pyrazin-2-yloxy)-benzyl]-oxazolidin-4-one;
2-(2,6-Dimethoxy-phenyl)-5,5-dimethyl-3-[4-(6-methyl-pyridazin-3-yloxy)-benzyl]-oxazolidin-4-one;

2-(2,6-Dimethoxy-phenyl)-5,5-dimethyl-3-[4-(thiazol-2-yloxy)-benzyl]-oxazolidin-4-one;
2-(2,6-Dimethoxy-phenyl)-5,5-dimethyl-3-[4-(pyrimidin-2-yloxy)-benzyl]-oxazolidin-4-one;
2-(2-Isopropoxy-6-methoxy-phenyl)-5,5-dimethyl-3-(4-phenoxy-benzyl)-oxazolidin-4-one;
2-(2-Ethoxy-6-methoxy-phenyl)-5,5-dimethyl-3-(4-phenoxy-benzyl)-oxazolidin-4-one;
2-[2-Methoxy-6-(2-methoxy-ethoxy)-phenyl]-5,5-dimethyl-3-(4-phenoxy-benzyl)-oxazolidin-4-one; and
2-[2-(3-Hydroxy-propoxy)-6-methoxy-phenyl]-5,5-dimethyl-3-(4-phenoxy-benzyl)-oxazolidin-4-one.

The compounds of formulae (I) and (II) and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formulae (I) and (II).

For avoidance of any doubt, if compounds are described as useful for the prevention or treatment of certain diseases, such compounds are likewise suitable for use in the preparation of a medicament for the prevention or treatment of said diseases.

The compounds according to formulae (I) and (II) are useful for the prevention or treatment of diseases related to the orexin system.

Such diseases related to the orexin system may be selected from the group consisting of all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

In a sub-embodiment, such diseases related to the orexin system may be selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders (notably all types of insomnias, especially primary insomnia).

In another sub-embodiment, such diseases related to the orexin system may be selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another sub-embodiment, such diseases related to the orexin system may be selected from the group consisting of eating disorders that comprise metabolic dysfunction; dysregulated appetite control; compulsive obesities; emeto-bulimia or anorexia nervosa.

In another sub-embodiment, such diseases related to the orexin system may be selected from the group consisting of all types of addictions (especially psychoactive substance use, abuse, seeking and reinstatement) that comprise all types of psychological or physical addictions and their related tolerance and dependence components.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders.

Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance.

Addictions may be defined as addiction to one or more rewarding stimuli, notably to one rewarding stimulus. Such rewarding stimuli may be of either natural or synthetic origin. Psychoactive substance use, abuse, seeking and reinstatement are defined as all types of psychological or physical addictions and their related tolerance and dependence components.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

Besides, any characteristics described in this invention for the compounds of formula (I) (whether for the compounds themselves, salts thereof, compositions containing the compounds or salts thereof, uses of the compounds or salts thereof, etc.) apply mutatis mutandis to compounds of formula ($I_{E1}$), formula ($I_{E2}$), and formula (II).

Preparation of Compounds of Formula (I):

A further aspect of the invention is a process for the preparation of compounds of formula (I). Compounds according to formula (I) of the present invention can be prepared according to the general sequence of reactions outlined in the schemes below wherein Y, $R^1$, $R^2$, $R^3$, $R^4$, $R^{15}$, $R^{16}$, $R^{17}$, and $R^{18}$ are as defined for formula (I) or (II). Other abbreviations used herein are explicitly defined, or are as defined in the experimental section. In some instances the generic groups Y, $R^1$, $R^2$, $R^3$, $R^4$, $R^{15}$, $R^{16}$, $R^{17}$, and $R^{18}$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into pharmaceutically acceptable salts thereof in a manner known per se.

In general, all chemical transformations can be performed according to well-known standard methodologies as described in the literature or as described in the procedures below.

Oxazolidin-4-one derivatives (Y is $CH_2$ or $CHR^1$) of formula (I) may be prepared according to scheme 1.

Scheme 1: Preparation of compounds of formula (I) wherein Y is $CH_2$ or $CHR^1$

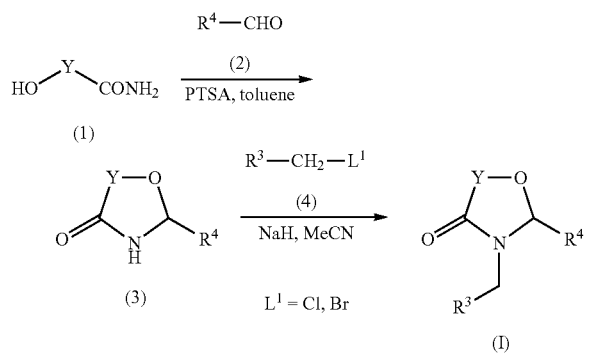

Condensation of an amide (1) with an aldehyde (2) in the presence of an acid such PTSA in a Dean-Stark apparatus and in a solvent such as toluene provided the oxazolidin-4-one derivatives (3). Alkylation with a halide (4) in the presence of a strong base such as NaH in an aprotic solvent such as DMF yields the final compounds of formula (I).

Oxazolidin-4-one derivatives (Y is $CR^1R^2$) of formula (I) may be prepared according to scheme 2.

Scheme 2: Preparation of compounds of formula (I) wherein Y is $CR^1R^2$

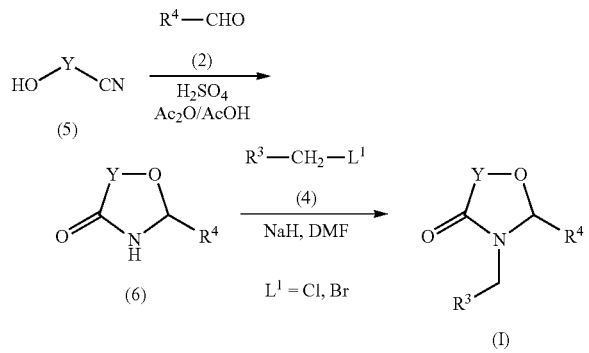

Alternatively, condensation of cyanhydrin (5) with an aldehyde (2) in the presence of an strong acid such sulfuric acid in a mixture of $Ac_2O$ and AcOH provides for example 5,5'-dimethyl-oxazolidin-4-one derivatives (6) (Stambach J.-P. et al, *Heterocycles*, 1997, 45, 9, 1825-1831). Alkylation with a halide (4) in the presence of a strong base such as NaH in an aprotic solvent such as DMF yields the compounds of formula (I).

Halides of formula $R^3$—$CH_2$-$L^1$ and aldehydes of formula $R^4$—CHO are commercially available, well known in the art, or readily available from commercially available precursors. Procedures to transform precursor functional groups into such required halides or aldehydes, such as reduction of carboxylic acids, esters, amides, nitriles; oxidation of alcohols; transformation into halides or equivalent activated alcohols (eg. methane-/toluene-sulphonates); or sequential metallation/formylation of aromatic halides are well known in the art (literature for precursors of heteroaryl-containing groups: see e.g. T. Eicher, S. Hauptmann "The chemistry of Heterocycles: Structure, Reactions, Syntheses, and Applications", 2nd Edition 2003, Wiley, ISBN 978-3-527-30720-3; A. R. Katrizky, C. W. Rees, E. F. V. Scriven (Eds.) "Comprehensive Heterocyclic Chemistry II" 1996, Elsevier, ISBN 0-08-042072-9).

In some instances, substituents may also be introduced in a final step onto an appropriate (eg. phenolic) precursor molecule. The hydroxy group of such phenol precursor may be alkylated using standard procedures, or arylated using standard procedures such as the Ullmann reaction with halide derivatives of formula $Ar^3$-$L^1$ in the presence of CuCl, 2,2,6,6-tetramethyl-heptane-3,5-dione and a base such as $Cs_2CO_3$ in an aprotic solvent such as NMP (WO2006/0173049).

The synthesis of some particular aldehydes of formula $R^4$—CHO is described in the following schemes 3 to 6.

Methylation of commercially available 2,3-dihydro-benzo[1,4]dioxin-6-ol (7) with dimethyl sulfate gives 6-methoxy-2,3-dihydro-benzo[1,4]dioxine (8) (Guillaumet G. et al. *Eur. J. Med. Chem.* 1990, 25, 1, 45-51). Formylation with n-BuLi/DMF in the presence of TMDA in an aprotic solvent such as THF affords the aldehyde (9) (Guillaumet G. et al. *J. Heterocyclic. Chem.* 1989, 26, 1, 193-197).

Methylation of commercially benzo[1,3]dioxol-5-ol (10) with methyl iodide in the presence of a base such as $K_2CO_3$ in an aprotic solvent such as acetone affords 5-methoxy-benzo[1,3]dioxole (11) (Schuda P. F. et al, *J. Org. Chem.* 1987, 52, 10, 1972-1979). Formylation with n-BuLi/DMF in the presence of TMDA in an aprotic solvent such as THF affords aldehyde (12) (Guillaumet G. et al. *J. Heterocyclic. Chem.* 1989, 26, 1, 193-197).

Riemer-Tiemann reaction with $CHCl_3$ in aq. NaOH of the commercially available 7-hydroxyquinoline (13) gives the aldehyde (14). Methylation with dimethyl sulfate affords 7-methoxy-quinoline-8-carbaldehyde (15) (U.S. Pat. No. 4,342,771).

Scheme 3: Preparation of 6-methoxy-2,3-dihydro-benzo[1,4]dioxine-5-carbaldehyde (9), 5-methoxy-benzo[1,3]dioxole-4-carbaldehyde (12) and 7-methoxy-quinoline-8-carbaldehyde (15).

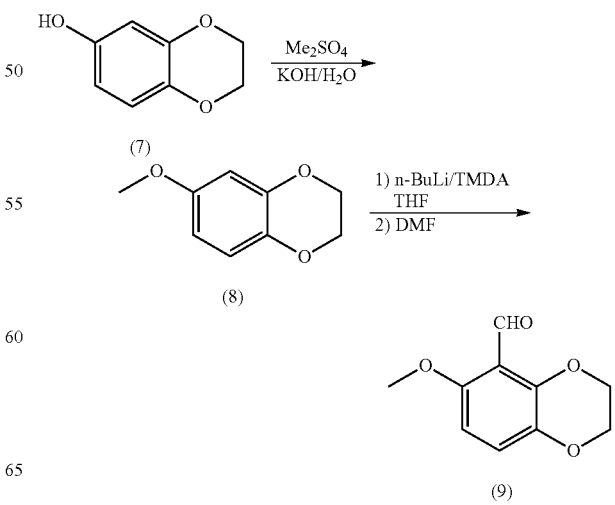

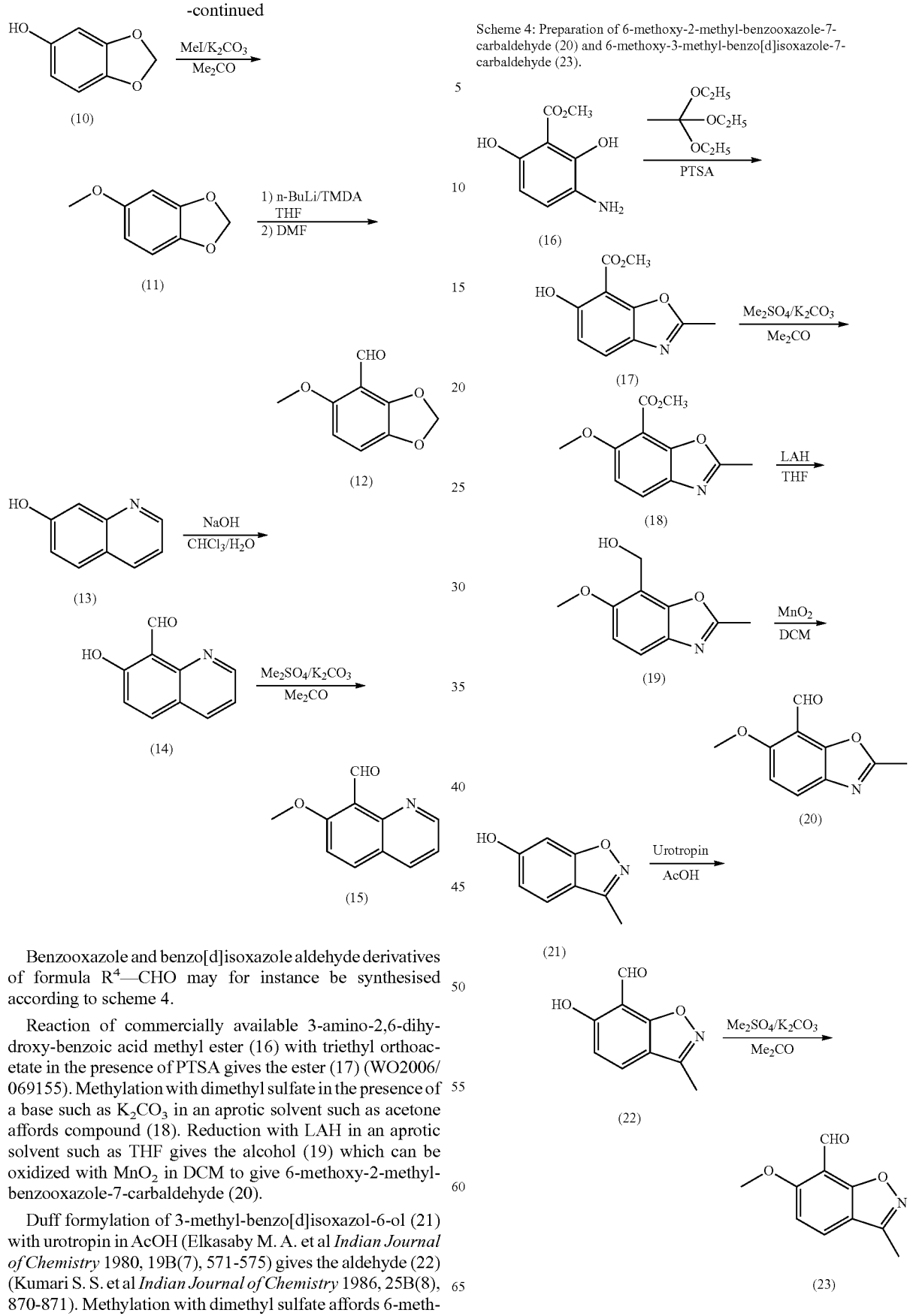

Benzooxazole and benzo[d]isoxazole aldehyde derivatives of formula $R^4$—CHO may for instance be synthesised according to scheme 4.

Reaction of commercially available 3-amino-2,6-dihydroxy-benzoic acid methyl ester (16) with triethyl orthoacetate in the presence of PTSA gives the ester (17) (WO2006/069155). Methylation with dimethyl sulfate in the presence of a base such as $K_2CO_3$ in an aprotic solvent such as acetone affords compound (18). Reduction with LAH in an aprotic solvent such as THF gives the alcohol (19) which can be oxidized with $MnO_2$ in DCM to give 6-methoxy-2-methyl-benzooxazole-7-carbaldehyde (20).

Duff formylation of 3-methyl-benzo[d]isoxazol-6-ol (21) with urotropin in AcOH (Elkasaby M. A. et al *Indian Journal of Chemistry* 1980, 19B(7), 571-575) gives the aldehyde (22) (Kumari S. S. et al *Indian Journal of Chemistry* 1986, 25B(8), 870-871). Methylation with dimethyl sulfate affords 6-methoxy-3-methyl-benzo[d]isoxazole-7-carbaldehyde (23).

Further synthetic methods for the preparation of aldehydes R⁴—CHO are described below for the specific examples shown in schemes 5 and 6.

Scheme 5: Preparation of 3,5-dimethoxy-pyridine-4-carbaldehyde (25) and 2,4-dimethoxy-pyrdine-3-carbaldehyde (27).

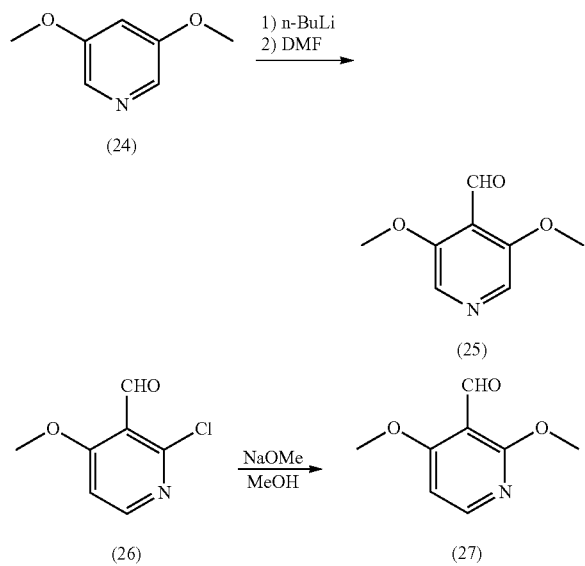

Formylation with n-BuLi/DMF in an aprotic solvent such as THF of the commercially available 3,5-dimethoxypyridine (21) affords 3,5-dimethoxy-pyridine-4-carbaldehyde (22) (U.S. Pat. No. 6,555,557).

Reaction of the commercially available 2-chloro-4-methoxy-pyridine-3-carbaldehyde (23) with NaOMe in MeOH affords 2,4-dimethoxy-pyridine-3-carbaldehyde (24).

Scheme 6: Preparation of 2-ethoxy-6-methoxy-benzaldehyde (29) and 4-fluoro-2,6-dimethoxy-benzaldehyde (31)

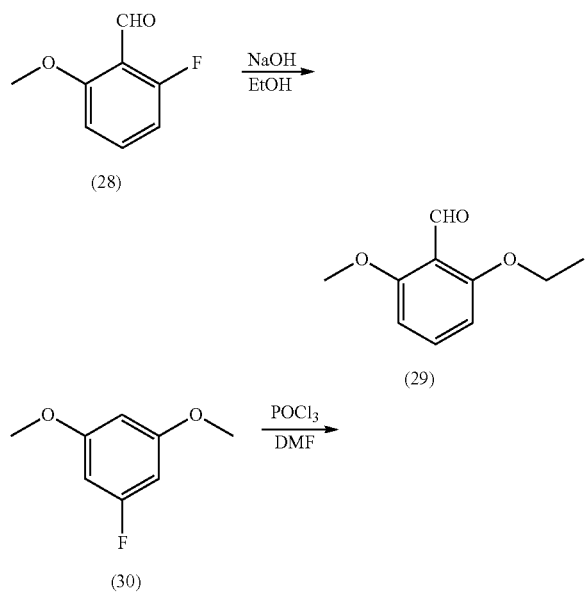

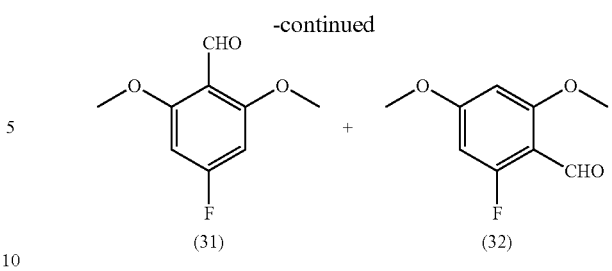

Reaction of commercially 2-fluoro-6-methoxy-benzaldehyde (28) with NaOH in EtOH affords the aldehyde (29) (U.S. Pat. No. 4,367,234).

Vilsmeier-Haack reaction with POCl₃ in dry DMF of commercially available 1-fluoro-3,5-dimethoxy-benzene (30) gives a mixture of aldehyde (31) and aldehyde (32) with a ratio of about 1/9 (Stanjeck V. et al. *Helvetica Chimica Acta* 1998, 81, 9, 1596-1607).

Whenever the compounds of formula (I) or (II) are obtained in the form of mixtures of enantiomers, the enantiomers can be separated using methods known to the one skilled in the art: e.g. by formation and separation of diastereomeric salts or by HPLC over a chiral stationary phase such as a Regis Whelk-O1 (R,R) (10 μm) column, a Daicel Chiral-Cel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

EXPERIMENTAL SECTION

Abbreviations (as Used Herein)

Ac acetyl (as in Ac₂O=acetic acid anhydride; AcOH=acetic acid)
aq. aqueous
Bn benzyl
BSA bovine serum albumine
CHO Chinese hamster ovary
conc. concentrated
d day(s)
DCM dichloromethane
DMF N,N-dimethylformamide
eq equivalent(s)
ES electron spray
ether diethyl ether
EtOAc ethyl acetate
FC flash chromatography on silica gel
FCS foatal calf serum
FLIPR fluorescent imaging plate reader
h hour(s)
HBSS Hank's balanced salt solution
HEPES 4-(2-hydroxyethyl)-piperazine-1-ethanesulfonic acid
HPLC high performance liquid chromatography
LAH lithium aluminium hydride
LC liquid chromatography
M molar(ity)
Me methyl
MeCN acetonitrile
MeOH methanol
min minute(s)
MS mass spectroscopy
MW microwave
n-BuLi n-butyllithium NMP 1-methyl-2-pyrrolidone
prep. preparative
PTSA (para-) p-toluenesulfonic acid
RT room temperature
sat. saturated
$t_R$ retention time
TBS tert-Butyldimethylsilyl
TFA trifluoroacetic acid
THF tetrahydrofuran
TMDA N,N,N',N'-tetramethylethylenediamine
I-Chemistry All temperatures are stated in ° C. Compounds are characterized by LC-MS (Finnigan Navigator with HP 1100 Binary Pump and DAD, column: 4.6×50 mm, Zorbax SB-AQ, 5 µm, 120 Å, using two conditions:

basic: eluent A: MeCN, eluent B: conc. $NH_3$ in water (1.0 mL/L), 5% to 95% $CH_3CN$;

acidic: eluent A: MeCN, eluent B: TFA in water (0.4 mL/L), 5% to 95% $CH_3CN$), $t_R$ is given in min; by TLC (TLC-plates from Merck, Silica gel 60 $F_{254}$); or by melting point. Compounds are purified by column chromatography on silica gel or by preparative HPLC (column: X-terra RP18, 50×19 mm, 5 µm, gradient: 10-95% MeCN in water containing 0.5% of formic acid).

The following examples illustrate the preparation of pharmacologically active compounds of the invention but do not at all limit the scope thereof. All example compounds have been synthesized in racemic form or as epimers without control of the stereocenter in position 2 of the oxazolidinone moiety.

A.1 Synthesis of oxazolidin-4-one derivatives

A.1.1 Synthesis of 2-aryl-oxazolidin-4-one derivatives (Y=$CH_2$ or $CHR^1$) (general procedure)

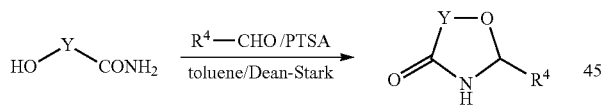

A mixture of the respective aldehyde derivative $R^4$—CHO (1.1 eq), the respective amide (1.0 eq), and PTSA (0.01 eq) in dry toluene (60 mL/20 mmol) is stirred at reflux in a Dean-Stark apparatus for 12 h. After removal of the toluene, the residue is dissolved in DCM, washed with water and brine, dried over $MgSO_4$ and concentrated in vacuo to give a crude oil. FC (EtOAc) gives the desired 4-aryl-oxazolidin-4-one derivative.

2-(2,6-Dimethoxy-phenyl)-oxazolidin-4-one prepared by reaction of 2,6-dimethoxybenzaldehyde with glycolamide; LC-MS: $t_R$=0.41 min; $[M+H]^+$=224.31.

2-(2-Ethoxy-phenyl)-oxazolidin-4-one prepared by reaction of 2-ethoxybenzaldehyde with glycolamide; LC-MS: $t_R$=0.75 min; $[M+H]^+$=207.97.

2-(2,6-Dimethoxy-phenyl)-(S)-5-methyl-oxazolidin-4-one prepared by reaction of 2,6-dimethoxybenzaldehyde with (S)-(−)-2-hydroxypropionamide; LC-MS: $t_R$=0.45 min; $[M+H]^+$=238.28.

2-(2,6-Dimethoxy-phenyl)-(R)-5-methyl-oxazolidin-4-one prepared by reaction of 2,6-dimethoxybenzaldehyde with (R)-(+)-lactamide; LC-MS: $t_R$=0.45 min; $[M+H]^+$=238.21.

A.1.2 Synthesis of 2-aryl-oxazolidin-4-one derivatives (Y=$CR^1R^2$)

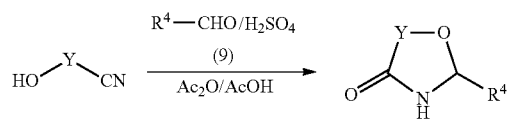

2-(2,6-Dimethoxy-phenyl)-5,5-dimethyl-oxazolidin-4-one

To a mixture of acetone cyanhydrin (851 mg), 2,6-dimethoxybenzaldehyde (1.58 g) in AcOH (10 mL) is added at 10° C. dropwise $H_2SO_4$ (1 mL) and $Ac_2O$ (0.5 mL). The reaction mixture is stirred at 10° C. for 40 min and then 10 min at RT. The reaction mixture is poured into cracked ice and extracted three times with ether. The combined organic extracts are washed with 10% aq. $NaHCO_3$, dried ($Na_2SO_4$), filtered and concentrated to yield a crude oil. FC (EtOAc) gives the title compound as a brown oil (1.3 g, 52%). LC-MS: $t_R$=0.47 min; $[M+H]^+$=252.25.

A.2 Preparation of Examples (Method A)

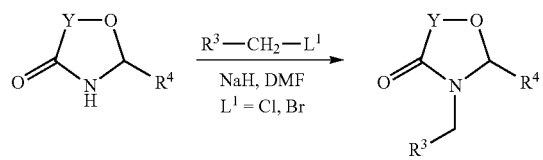

To a cold (0° C.) solution of the respective 2-substituted oxazolidin-4-one derivative (1.0 eq) in DMF (1 mL/0.1 mmol) is added NaH (50% in mineral oil) (2 eq). The reaction mixture is stirred at RT for 30 min under inert atmosphere. Then the respective halide (1 eq) is added and the reaction mixture is stirred at 70° C. for 1.5 h and then 12 h at RT. The products are directly purified by prep. HPLC to provide the final compounds.

The Examples given in table 1 were synthesized according to method A above:

TABLE 1

| Example | Name | [M + H]+ | $t_R$ |
|---|---|---|---|
| 1 | 3-(4-Chloro-3-trifluoromethyl-benzyl)-2-(2-ethoxy-phenyl)-oxazolidin-4-one | 399.97 | 1.11 |
| 2 | 2-(2-Ethoxy-phenyl)-3-(2-methyl-benzyl)-oxazolidin-4-one | 311.96 | 0.98 |
| 3 | 2-(2-Ethoxy-phenyl)-3-(4-trifluoromethyl-benzyl)-oxazolidin-4-one | 365.97 | 1.09 |
| 4 | 2-(2-Ethoxy-phenyl)-3-(3-methoxy-benzyl)-oxazolidin-4-one | 327.98 | 0.95 |
| 5 | 2-(2-Ethoxy-phenyl)-3-(3-trifluoromethyl-benzyl)-oxazolidin-4-one | 366.01 | 1.08 |
| 6 | 2-(2-Ethoxy-phenyl)-3-(4-trifluoromethoxy-benzyl)-oxazolidin-4-one | 381.97 | 1.09 |
| 7 | 2-(2-Ethoxy-phenyl)-3-(3-trifluoromethoxy-benzyl)-oxazolidin-4-one | 382.02 | 1.09 |
| 8 | 2-(2-Ethoxy-phenyl)-3-(4-fluoro-3-methyl-benzyl)-oxazolidin-4-one | 329.97 | 1.00 |
| 9 | 3-(3-Chloro-4-fluoro-benzyl)-2-(2-ethoxy-phenyl)-oxazolidin-4-one | 349.96 | 1.07 |
| 10 | 3-(3-Chloro-2-fluoro-5-trifluoromethyl-benzyl)-2-(2-ethoxy-phenyl)-oxazolidin-4-one | 417.90 | 1.13 |
| 11 | 2-(2-Ethoxy-phenyl)-3-(2-methyl-3-trifluoromethyl-benzyl)-oxazolidin-4-one | 380.04 | 1.11 |
| 12 | 3-(2-Chloro-5-trifluoromethyl-benzyl)-2-(2-ethoxy-phenyl)-oxazolidin-4-one | 399.96 | 1.12 |
| 13 | 2-(2-Ethoxy-phenyl)-3-(2-fluoro-5-trifluoromethyl-benzyl)-oxazolidin-4-one | 384 | 1.09 |
| 14 | 2-(2-Ethoxy-phenyl)-3-(4-fluoro-3-trifluoromethyl-benzyl)-oxazolidin-4-one | 384 | 1.09 |
| 15 | 2-(2-Ethoxy-phenyl)-3-(3-fluoro-4-trifluoromethyl-benzyl)-oxazolidin-4-one | 384 | 1.10 |
| 16 | 3-(2-Chloro-3,6-difluoro-benzyl)-2-(2-ethoxy-phenyl)-oxazolidin-4-one | 367.96 | 1.07 |
| 17 | 3-(4-Chloro-3-fluoro-benzyl)-2-(2-ethoxy-phenyl)-oxazolidin-4-one | 349.95 | 1.08 |
| 18 | 3-(3-Chloro-4-trifluoromethoxy-benzyl)-2-(2-ethoxy-phenyl)-oxazolidin-4-one | 415.95 | 1.12 |
| 19 | 3-(4-Chloro-2-fluoro-benzyl)-2-(2-ethoxy-phenyl)-oxazolidin-4-one | 349.94 | 1.08 |
| 20 | 2-(2-Ethoxy-phenyl)-3-(2-fluoro-benzyl)-oxazolidin-4-one | 315.97 | 1.04 |
| 21 | 3-(4-Chloro-benzyl)-2-(2-ethoxy-phenyl)-oxazolidin-4-one | 331.94 | 1.07 |
| 22 | 2-(2-Ethoxy-phenyl)-3-(2-fluoro-4-trifluoromethyl-benzyl)-oxazolidin-4-one | 384.02 | 1.10 |
| 23 | 3-(2,6-Dichloro-benzyl)-2-(2-ethoxy-phenyl)-oxazolidin-4-one | 365.93 | 1.09 |
| 24 | 2-(2-Ethoxy-phenyl)-3-(3-methyl-benzyl)-oxazolidin-4-one | 311.96 | 0.99 |
| 25 | 2-(2-Ethoxy-phenyl)-3-(4-fluoro-benzyl)-oxazolidin-4-one | 315.98 | 0.97 |
| 26 | 3-(3,4-Difluoro-benzyl)-2-(2-ethoxy-phenyl)-oxazolidin-4-one | 333.97 | 1.05 |
| 27 | 2-(2-Ethoxy-phenyl)-3-(4-methoxy-benzyl)-oxazolidin-4-one | 327.99 | 0.96 |
| 28 | 2-(2-Ethoxy-phenyl)-3-(5-methyl-2-trifluoromethyl-benzyl)-oxazolidin-4-one | 380.02 | 1.11 |
| 29 | 3-(3,4-Dichloro-benzyl)-2-(2-ethoxy-phenyl)-oxazolidin-4-one | 365.93 | 1.10 |
| 30 | 3-(2,4-Dichloro-benzyl)-2-(2-ethoxy-phenyl)-oxazolidin-4-one | 365.95 | 1.11 |
| 31 | 3-(3-Chloro-4-methyl-benzyl)-2-(2-ethoxy-phenyl)-oxazolidin-4-one | 345.95 | 1.09 |
| 32 | 2-(2,6-Dimethoxy-phenyl)-3-(4-trifluoromethyl-benzyl)-oxazolidin-4-one | 381.99 | 1.06 |
| 33 | 2-(2,6-Dimethoxy-phenyl)-3-(2-trifluoromethoxy-benzyl)-oxazolidin-4-one | 397.97 | 1.07 |
| 34 | 2-(2,6-Dimethoxy-phenyl)-3-(4-trifluoromethoxy-benzyl)-oxazolidin-4-one | 397.97 | 1.07 |
| 35 | 2-(2,6-Dimethoxy-phenyl)-3-(3-trifluoromethoxy-benzyl)-oxazolidin-4-one | 397.97 | 1.07 |
| 36 | 3-(3-Chloro-4-fluoro-benzyl)-2-(2,6-dimethoxy-phenyl)-oxazolidin-4-one | 365.95 | 1.05 |
| 37 | 3-(3-Chloro-2-fluoro-5-trifluoromethyl-benzyl)-2-(2,6-dimethoxy-phenyl)-oxazolidin-4-one | 433.90 | 1.10 |
| 38 | 2-(2,6-Dimethoxy-phenyl)-3-(4-fluoro-3-trifluoromethyl-benzyl)-oxazolidin-4-one | 400.02 | 1.06 |
| 39 | 3-(4-Chloro-3-fluoro-benzyl)-2-(2,6-dimethoxy-phenyl)-oxazolidin-4-one | 365.96 | 1.05 |

TABLE 1-continued

| Example | Name | [M + H]⁺ | $t_R$ |
|---|---|---|---|
| 40 | 3-(3-Chloro-4-trifluoromethoxy-benzyl)-2-(2,6-dimethoxy-phenyl)-oxazolidin-4-one | 431.91 | 1.10 |
| 41 | 2-(2,6-Dimethoxy-phenyl)-3-(2,4,6-trimethyl-benzyl)-oxazolidin-4-one | 356.04 | 1.01 |
| 42 | 3-(2,4-Dichloro-benzyl)-2-(2,6-dimethoxy-phenyl)-oxazolidin-4-one | 381.91 | 1.01 |
| 43 | 3-(3-Chloro-4-methyl-benzyl)-2-(2,6-dimethoxy-phenyl)-oxazolidin-4-one | 341.99 | 1.05 |
| 44 | 2-(2,6-Dimethoxy-phenyl)-3-(2,6-dimethyl-benzyl)-oxazolidin-4-one | 341.94 | 1.16 |
| 45 | 3-(2-Chloro-benzyl)-2-(2-ethoxy-phenyl)-oxazolidin-4-one | 331.92 | 1.06 |
| 46 | 3-(2,5-Dichloro-benzyl)-2-(2-ethoxy-phenyl)-oxazolidin-4-one | 365.95 | 1.11 |
| 47 | 2-(2,6-Dimethoxy-phenyl)-3-(4-phenoxy-benzyl)-oxazolidin-4-one | 406.13 | 0.78 |
| 48 | 2-(2,6-Dimethoxy-phenyl)-3-(3-fluoro-4-trifluoromethoxy-benzyl)-oxazolidin-4-one | 416.13 | 0.76 |
| 49 | 3-(4-Difluoromethoxy-benzyl)-2-(2,6-dimethoxy-phenyl)-oxazolidin-4-one | 380.17 | 0.70 |
| 50 | 2-(2,6-Dimethoxy-phenyl)-5,5-dimethyl-3-(4-phenoxy-benzyl)-oxazolidin-4-one | 433.78 | 0.80 |
| 51 | 2-(2,6-Dimethoxy-phenyl)-(R)-5-methyl-3-(4-phenoxy-benzyl)-oxazolidin-4-one | 420.19 | 0.79 |
| 52 | 3-(4-Difluoromethoxy-benzyl)-2-(2,6-dimethoxy-phenyl)-(R)-5-methyl-oxazolidin-4-one | 394.16 | 0.72 |
| 53 | 2-(2,6-Dimethoxy-phenyl)-(R)-5-methyl-3-naphthalen-2-ylmethyl-oxazolidin-4-one | 378.29 | 0.75 |
| 54 | 2-(2,6-Dimethoxy-phenyl)-3-(4-propoxy-benzyl)-oxazolidin-4-one | 372.20 | 0.74 |
| 55 | 2-(2,6-Dimethoxy-phenyl)-3-(3-fluoro-4-trifluoromethoxy-benzyl)-(R)-5-methyl-oxazolidin-4-one | 430.14 | 0.77 |
| 56 | 3-(3-Chloro-4-trifluoromethoxy-benzyl)-2-(2,6-dimethoxy-phenyl)-(R)-5-methyl-oxazolidin-4-one | 446.14 | 0.79 |
| 57 | 2-(2,6-Dimethoxy-phenyl)-5,5-dimethyl-3-naphthalen-2-ylmethyl-oxazolidin-4-one | 392.24 | 0.76 |
| 58 | 3-(3-Chloro-4-trifluoromethoxy-benzyl)-2-(2,6-dimethoxy-phenyl)-5,5-dimethyl-oxazolidin-4-one | 460.11 | 0.81 |
| 59 | 2-(2,6-Dimethoxy-phenyl)-(S)-5-methyl-3-(4-phenoxy-benzyl)-oxazolidin-4-one | 420.22 | 0.79 |
| 60 | 2-(2,6-Dimethoxy-phenyl)-3-(4-isopropoxy-benzyl)-oxazolidin-4-one | 372.22 | 0.72 |
| 61 | 2-(2,6-Dimethoxy-phenyl)-5,5-dimethyl-3-(4-trifluoromethoxy-benzyl)-oxazolidin-4-one | 426.24 | 0.78 |
| 62 | 3-Benzothiazol-2-ylmethyl-2-(2,6-dimethoxy-phenyl)-(R)-5-methyl-oxazolidin-4-one | 385.12 | 0.68 |
| 63 | 2-(2,6-Dimethoxy-phenyl)-(R)-5-methyl-3-(4-trifluoromethoxy-benzyl)-oxazolidin-4-one | 412.22 | 0.77 |
| 64 | 3-Benzothiazol-2-ylmethyl-2-(2,6-dimethoxy-phenyl)-5,5-dimethyl-oxazolidin-4-one | 399.21 | 0.70 |
| 65 | 3-(4-Cyclopropylmethoxy-benzyl)-2-(2,6-dimethoxy-phenyl)-oxazolidin-4-one | 384.28 | 0.74 |
| 66 | 2-(2,6-Dimethoxy-phenyl)-(S)-5-methyl-3-naphthalen-2-ylmethyl-oxazolidin-4-one | 378.19 | 0.75 |
| 67 | 2-(2,6-Dimethoxy-phenyl)-3-(3-fluoro-4-trifluoromethoxy-benzyl)-5,5-dimethyl-oxazolidin-4-one | 444.13 | 0.79 |
| 68 | 3-Benzooxazol-2-ylmethyl-2-(2,6-dimethoxy-phenyl)-5,5-dimethyl-oxazolidin-4-one | 383.20 | 0.67 |
| 69 | 3-(4-Difluoromethoxy-benzyl)-2-(2,6-dimethoxy-phenyl)-5,5-dimethyl-oxazolidin-4-one | 408.19 | 0.74 |
| 70 | 2-(2,6-Dimethoxy-phenyl)-5,5-dimethyl-3-(1-methyl-1H-benzoimidazol-2-ylmethyl)-oxazolidin-4-one | 396.22 | 0.51 |
| 71 | 3-Benzo[1,3]dioxol-5-ylmethyl-2-(2,6-dimethoxy-phenyl)-5,5-dimethyl-oxazolidin-4-one | 385.73 | 0.69 |
| 72 | 2-(2,6-Dimethoxy-phenyl)-3-(4-methoxy-benzyl)-5,5-dimethyl-oxazolidin-4-one | 372.22 | 0.69 |
| 73 | 2-(2,6-Dimethoxy-phenyl)-(R)-5-methyl-3-(4-propoxy-benzyl)-oxazolidin-4-one | 385.83 | 0.76 |
| 74 | 2-(2,6-Dimethoxy-phenyl)-3-(4-isopropoxy-benzyl)-(R)-5-methyl-oxazolidin-4-one | 385.82 | 0.74 |
| 75 | 3-(4-Cyclopropylmethoxy-benzyl)-2-(2,6-dimethoxy-phenyl)-(R)-5-methyl-oxazolidin-4-one | 398.27 | 0.75 |
| 76 | 2-(2,6-Dimethoxy-phenyl)-3-(4-isopropoxy-benzyl)-5,5-dimethyl-oxazolidin-4-one | 400.27 | 0.75 |

TABLE 1-continued

| Example | Name | [M + H]⁺ | $t_R$ |
|---|---|---|---|
| 77 | 2-(2,6-Dimethoxy-phenyl)-5,5-dimethyl-3-(4-propoxy-benzyl)-oxazolidin-4-one | 400.27 | 0.77 |
| 78 | 3-(4-Cyclopropylmethoxy-benzyl)-2-(2,6-dimethoxy-phenyl)-5,5-dimethyl-oxazolidin-4-one | 412.23 | 0.76 |
| 79 | 2-(2,6-Dimethoxy-phenyl)-3-(4-ethoxy-benzyl)-(r)-5-methyl-oxazolidin-4-one | 372.23 | 0.71 |
| 80 | 2-(2,6-Dimethoxy-phenyl)-3-(4-ethoxy-benzyl)-5,5-dimethyl-oxazolidin-4-one | 385.76 | 0.73 |
| 81 | 3-(3-Chloro-4-trifluoromethoxy-benzyl)-2-(2,6-dimethoxy-phenyl)-5,5-dimethyl-oxazolidin-4-one | 428.09 | 0.86 |
| 82 | 3-(3-Chloro-4-trifluoromethoxy-benzyl)-2-(2,6-difluoro-phenyl)-5,5-dimethyl-oxazolidin-4-one | 436.07 | 0.83 |
| 83 | 3-(3-Chloro-4-trifluoromethoxy-benzyl)-2-(2-methoxy-6-methyl-phenyl)-5,5-dimethyl-oxazolidin-4-one | 443.31 | 0.86 |
| 84 | 2-(2-Fluoro-6-methoxy-phenyl)-5,5-dimethyl-3-(4-phenoxy-benzyl)-oxazolidin-4-one | 422.20 | 0.82 |
| 85 | 2-(2-Chloro-6-methoxy-phenyl)-5,5-dimethyl-3-(4-phenoxy-benzyl)-oxazolidin-4-one | 438.19 | 0.83 |
| 86 | 2-(2-Methoxy-6-trifluoromethyl-phenyl)-5,5-dimethyl-3-(4-phenoxy-benzyl)-oxazolidin-4-one | 472.25 | 0.85 |
| 87 | 3-Biphenyl-4-ylmethyl-2-(2,6-dimethoxy-phenyl)-5,5-dimethyl-oxazolidin-4-one | 417.77 | 0.81 |
| 88 | 2-(2,6-Dimethoxy-phenyl)-5,5-dimethyl-3-(4-trifluoromethylsulfanyl-benzyl)-oxazolidin-4-one | 442.17 | 0.81 |
| 89 | 2-(2,6-Dimethoxy-phenyl)-5,5-dimethyl-3-(6-phenoxy-pyridin-3-ylmethyl)-oxazolidin-4-one | 435.24 | 0.73 |

Example 90

2-(2,6-Dimethoxy-phenyl)-5,5-dimethyl-3-(5-phenoxy-pyridin-2-ylmethyl)-oxazolidin-4-one This compound has been prepared according to method A above using 2-chloromethyl-5-phenoxy-pyridine hydrochloride (prepared using the methods given in Kawasuji T. et al, *Bioorganic & Medicinal Chemistry* 2006, 14, 8430-8445 and WO2007/099317) as halide. LC-MS: $t_R$=0.72 min; [M+H]⁺=435.16.

A.3 Preparation of Examples (Method B)

A.3.1 Preparation of 2-(2,6-dimethoxy-phenyl)-3-(4-hydroxy-benzyl)-5,5-dimethyl-oxazolidin-4-one This compound has been prepared according to method A above using (4-bromomethyl-phenoxy)-tert-butyl-diphenyl-silane (prepared using the methods given in Petit G. R. et al, *Journal of Medicinal Chemistry* 2002, 45, 12, 2534-2542) as halide. LC-MS: $t_R$=0.58 min; [M+H]⁺=358.20.

A.3.2 Preparation of Examples (Method B)

The examples given in table 2 have been prepared from 2-(2,6-dimethoxy-phenyl)-3-(4-hydroxy-benzyl)-5,5-dimethyl-oxazolidin-4-one via Ullmann reaction with an appropriate heteroaryl halide derivatives of formula R¹⁵-L¹ in the presence of CuCl, 2,2,6,6-tetramethyl-heptane-3,5-dione and a base such as $Cs_2CO_3$ in an aprotic solvent such as NMP (WO2006/0173049).

TABLE 2

| Example | Name | [M + H]⁺ | $t_R$ |
|---|---|---|---|
| 91 | 2-(2,6-Dimethoxy-phenyl)-5,5-dimethyl-3-[4-(pyridin-2-yloxy)-benzyl]-oxazolidin-4-one | 435.28 | 0.73 |
| 92 | 2-(2,6-Dimethoxy-phenyl)-5,5-dimethyl-3-[4-(pyrazin-2-yloxy)-benzyl]-oxazolidin-4-one | 436.31 | 0.72 |
| 93 | 2-(2,6-Dimethoxy-phenyl)-5,5-dimethyl-3-[4-(6-methyl-pyridazin-3-yloxy)-benzyl]-oxazolidin-4-one | 449.71 | 0.64 |
| 94 | 2-(2,6-Dimethoxy-phenyl)-5,5-dimethyl-3-[4-(thiazol-2-yloxy)-benzyl]-oxazolidin-4-one | 441.18 | 0.73 |
| 95 | 2-(2,6-Dimethoxy-phenyl)-5,5-dimethyl-3-[4-(pyrimidin-2-yloxy)-benzyl]-oxazolidin-4-one | 436.24 | 0.68 |

A.4 Preparation of Examples (Method C)

A.4.1 Preparation of 2-(2-hydroxy-6-methoxy-phenyl)-5,5-dimethyl-3-(4-phenoxy-benzyl)-oxazolidin-4-one A.4.1.1. Preparation of 2-(2-benzyloxy-6-methoxy-phenyl)-5,5-dimethyl-oxazolidin-4-one A mixture of commercially available 2-hydroxyisobutyramide (638.5 mg, 3 eq), 2-benzyloxy-6-methoxy-benzaldehyde (500 mg) (Katritzky A. R. et al *ARKIVOC* 2001, 2, 3, 3-12) is heated at 240° C. for 5 min using microwave irradiation (Lecolier S. et al *Chimica Therapeutica* 1969, 4,6, 437-445). The crude oil is poured into water and extracted with DCM. The combined organic extracts are dried ($MgSO_4$), filtered and concentrated to yield a crude oil. FC (EN n-heptane: 1/1 to 1/0) gives the title compound as a yellow solid (0.41 g, 61%); LC-MS: $t_R$=0.65 min; [M+H]⁺=328.22.

A.4.1.2. Preparation of 2-(2-hydroxy-6-methoxy-phenyl)-5,5-dimethyl-oxazolidin-4-one To a cold (0° C.) solution of 2-(2-benzyloxy-6-methoxy-phenyl)-5,5-dimethyl-oxazolidin-4-one (410 mg) in dry DMF (5 mL) is added portionwise NaH 90% (45 mg, 1.5 eq). The reaction mixture is stirred for 15 min at 0° C. and then commercially available 1-(bromomethyl)-4-phenoxybenzene (395 mg, 1.2 eq) is added and the reaction mixture is stirred at RT for 1 h. The reaction mixture is poured into water, extracted with DCM. The combined organic extracts are dried (MgSO$_4$), filtered and concentrated to yield a crude oil. FC (EN n-heptane: 0/1 to 4/6) gives 2-(2-benzyloxy-6-methoxy-phenyl)-5,5-dimethyl-3-(4-phenoxy-benzyl)-oxazolidin-4-one as a colorless oil (0.495 g, 77%); LC-MS: $t_R$=0.88 min; [M+H]$^+$=510.33.

Hydrogenation of this intermediate over Pd(OH)$_2$ at normal pressure in EtOH gives the title compound as a white solid (388 mg, 93%); LC-MS: $t_R$=0.75 min; [M+H]$^+$=420.17.

A.4.2. Preparation of Examples (Method C)

To a mixture of 2-(2-hydroxy-6-methoxy-phenyl)-5,5-dimethyl-oxazolidin-4-one (0.05 mmol), Cs$_2$CO$_3$ (0.065 mmol) in dry DMF (0.1 mL) is added dropwise the appropriate halide alkylating agent (0.1 mmol) (e.g. 1-bromo-3-hydroxy-propane, 2-methoxy-ethylbromide, 2-bromopropane, ethylbromide) in dry DMF (0.1 mL). The reaction mixture is stirred at 90° C. for 30 min. The products are directly purified by prep. HPLC to provide the final compound.

The Examples given in table 3 were synthesized according to method C above:

TABLE 3

| Example | Name | [M + H]$^+$ | $t_R$ |
|---|---|---|---|
| 96 | 2-(2-Isopropoxy-6-methoxy-phenyl)-5,5-dimethyl-3-(4-phenoxy-benzyl)-oxazolidin-4-one | 462.24 | 1.04 |
| 97 | 2-(2-Ethoxy-6-methoxy-phenyl)-5,5-dimethyl-3-(4-phenoxy-benzyl)-oxazolidin-4-one | 448.19 | 1.01 |
| 98 | 2-[2-Methoxy-6-(2-methoxy-ethoxy)-phenyl]-5,5-dimethyl-3-(4-phenoxy-benzyl)-oxazolidin-4-one | 478.16 | 0.97 |
| 99 | 2-[2-(3-Hydroxy-propoxy)-6-methoxy-phenyl]-5,5-dimethyl-3-(4-phenoxy-benzyl)-oxazolidin-4-one | 478.15 | 0.90 |

II-Biological Assays
In Vitro Assay

The orexin receptor antagonistic activity of the compounds of formula (I) is determined in accordance with the following experimental method.

Chinese hamster ovary (CHO) cells expressing the human orexin-1 receptor and the human orexin-2 receptor, respectively, are grown in culture medium (Ham F-12 with L-Glutamine) containing 300 μg/ml G418, 100 U/ml penicillin, 100 μg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% CO$_2$.

Human orexin-A as an agonist is prepared as 1 mM stock solution in MeOH:water (1:1), diluted in HBSS containing 0.1% bovine serum albumin (BSA), NaHCO$_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), NaHCO$_3$: 0.375 g/l and 20 mM HEPES. On the day of the assay, 50 μl of staining buffer (HBSS containing 1% FCS, 20 mM HEPES, NaHCO$_3$: 0.375 g/l, 5 mM probenecid (Sigma) and 3 μM of the fluorescent calcium indicator fluo-4 AM (1 mM stock solution in DMSO, containing 10% pluronic) is added to each well. The 384-well cell-plates are incubated for 50 min at 37° C. in 5% CO$_2$ followed by equilibration at rt for 30-120 min before measurement.

Within the Fluorescent Imaging Plate Reader (FLIPR Tetra, Molecular Devices), antagonists are added to the plate in a volume of 10 μl/well, incubated for 10 min and finally 10 μl/well of agonist is added. Fluorescence is measured for each well at 1 second intervals, and the height of each fluorescence peak is compared to the height of the fluorescence peak induced by 3 nM orexin-A with vehicle in place of antagonist. For each antagonist, the IC$_{50}$ value (the concentration of compound needed to inhibit 50% of the agonistic response) is determined and normalized using the obtained IC$_{50}$ value of a on-plate reference compound. Optimized conditions were achieved by adjustment of pipetting speed and cell splitting regime. The calculated IC$_{50}$ values of the compounds may fluctuate depending on the daily cellular assay performance. Fluctuations of this kind are known to those skilled in the art.

Antagonistic activities of exemplified compounds are displayed in Table 1.

TABLE 1

| Ex. | OX$_1$ IC$_{50}$ (nM) | OX$_2$ IC$_{50}$ (nM) | Ex. | OX$_1$ IC$_{50}$ (nM) | OX$_2$ IC$_{50}$ (nM) | Ex. | OX$_1$ IC$_{50}$ (nM) | OX$_2$ IC$_{50}$ (nM) |
|---|---|---|---|---|---|---|---|---|
| 18 | 8794 | 26 | 1 | 6487 | 263 | 13 | >10000 | 290 |
| 37 | 162 | 477 | 2 | >10000 | 223 | 14 | >10000 | 169 |
| 40 | 198 | 29 | 3 | 9991 | 230 | 15 | >10000 | 359 |
| 47 | 1184 | 68 | 4 | >10000 | 705 | 16 | 590 | 3813 |
| 50 | 28* | 58* | 5 | >10000 | 462 | 17 | 9370 | 627 |
| 51 | 220 | 25 | 6 | >10000 | 55 | 19 | 9598 | 586 |
| 57 | 5*[2] | 151*[2] | 7 | 6806 | 74 | 20 | >10000 | 262 |
| 61 | 29 | 160 | 8 | 9167 | 584 | 21 | >10000 | 696 |
| 67 | 25*[2] | 322*[2] | 9 | 8736 | 79 | 22 | >10000 | 839 |
| 70 | 65 | 1298 | 10 | 8409 | 693 | 23 | 1844 | 787 |
| 76 | 114 | 193 | 11 | 5408 | 385 | 24 | >10000 | 363 |
| 80 | 139 | 1937 | 12 | 4044 | 590 | 68 | 2936 | 508 |
| 25 | >10000 | 199 | 38 | 1382 | 730 | 53 | 47 | 65 |
| 26 | >10000 | 652 | 39 | 4105 | 795 | 54 | 1710 | 81 |
| 27 | >10000 | 353 | 41 | 542 | 681 | 55 | 178 | 108 |
| 28 | 8021 | 661 | 42 | 1489 | 376 | 56 | 164 | 111 |
| 29 | >10000 | 696 | 43 | 553 | 349 | 58 | 25 | 133 |
| 30 | 3045 | 844 | 44 | 1758 | 467 | 59 | 2134 | 150 |
| 31 | 7596 | 634 | 45 | 1738 | 870 | 60 | 3242 | 159 |

TABLE 1-continued

| Ex. | OX$_1$ IC$_{50}$ (nM) | OX$_2$ IC$_{50}$ (nM) | Ex. | OX$_1$ IC$_{50}$ (nM) | OX$_2$ IC$_{50}$ (nM) | Ex. | OX$_1$ IC$_{50}$ (nM) | OX$_2$ IC$_{50}$ (nM) |
|---|---|---|---|---|---|---|---|---|
| 32 | >10000 | 413 | 46 | 788 | 1522 | 62 | 2867 | 193 |
| 33 | >10000 | 225 | 47 | 1184 | 68 | 63 | 260 | 216 |
| 34 | 6474 | 298 | 48 | 1352 | 99 | 64 | 411 | 222 |
| 35 | 2889 | 618 | 49 | 2991 | 113 | 65 | 6325 | 243 |
| 36 | 1340 | 632 | 52 | 726 | 41 | 66 | 421 | 266 |
| 69 | 187 | 928 | 82 | 336 | 110 | 92 | 1212 | 3059 |
| 71 | 150 | 1664 | 83 | 133 | 69 | 93 | 1198 | 8331 |
| 72 | 188 | 2267 | 84 | 421 | 46 | 95 | 2990 | 7262 |
| 73 | 581 | 86 | 85 | 204 | 37 | 96 | 10 | 120 |
| 74 | 1208 | 95 | 86 | 2177 | 65 | 97 | 25 | 62 |
| 75 | 1763 | 123 | 87 | 64 | 1086 | 98 | 345 | 366 |
| 77 | 114 | 484 | 88 | 120 | 298 | 99 | 80 | 150 |
| 78 | 472 | 620 | 89 | 139 | 212 | 81 | 920 | 88 |
| 79 | 830 | 864 | 90 | 413 | 236 | 91 | 110 | 443 |

Ex. = Compound of Example
*geomean from n = 5 values
*$^2$geomean from n = 2 values

The invention claimed is:
1. A compound of formula (I)

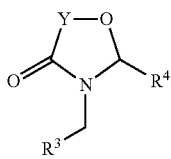

Formula (I)

wherein
Y represents CH$_2$, CHR$^1$, or CR$^1$R$^2$; wherein
R$^1$ and R$^2$ independently represent (C$_{1-4}$)alkyl;
R$^3$ represents Ar$^1$ or Ar$^3$—Z—Ar$^2$—* wherein the asterisk indicates the bond that is attached to the rest of the molecule; wherein
Ar$^1$ represents aryl or heteroaryl, wherein the aryl or heteroaryl is independently unsubstituted, or mono-, di-, or tri-substituted, wherein the substituents are independently selected from the group consisting of (C$_{1-4}$)alkyl, (C$_{1-4}$)alkoxy, halogen, (C$_{1-3}$)fluoroalkyl, (C$_{1-3}$)fluoroalkoxy, (C$_{1-3}$)fluoroalkyl-thio-, and (C$_{3-6}$)cycloalkyl-(C$_{1-4}$)alkoxy;
Ar$^2$ represents phenyl or 5- to 6-membered heteroaryl;
Z represents a bond, O, or —CH$_2$—O—* wherein the asterisk indicates the bond that is attached to Ar$^2$;
Ar$^3$ represents phenyl or 5- to 6-membered heteroaryl wherein the phenyl or 5- to 6-membered heteroaryl is independently unsubstituted, or mono-, di-, or tri-substituted, wherein the substituents are independently selected from the group consisting of (C$_{1-4}$) alkyl, (C$_{1-4}$)alkoxy, halogen, (C$_{1-3}$)fluoroalkyl, and (C$_{1-3}$) fluoroalkoxy; and
R$^4$ represents aryl or heteroaryl, wherein the aryl or heteroaryl is independently mono-, di-, or tri-substituted, wherein the substituents are independently selected from the group consisting of (C$_{1-4}$)alkyl, (C$_{1-4}$)alkoxy, halogen, (C$_{1-3}$)fluoroalkyl, (C$_{1-3}$)fluoroalkoxy, hydroxy-(C$_1$4alkoxy, and (C$_{1-4}$)alkoxy-(C$_{1-4}$)alkoxy; wherein, in the specific case wherein said aryl or heteroaryl is a bicyclic ring, the aryl or heteroaryl may also be unsubstituted;
with the exception of the following compounds:
2-(2-bromophenyl)-3-[(4-methoxyphenyl)methyl]-4-oxazolidinone;
2-(2-bromophenyl)-3-{[4-(trifluoromethyl)phenyl]methyl}-4-oxazolidinone;
2-(2-bromophenyl)-3-(phenylmethyl)-4-oxazolidinone; and
2-(4-methoxyphenyl)-3-[(4-methoxyphenyl)methyl]-5-methyl-4-oxazolidinone;
in a free or a pharmaceutically acceptable salt.
2. The compound according to claim 1; wherein Y represents CHR$^1$, or CR$^1$R$^2$;
in a free or a pharmaceutically acceptable salt.
3. The compound according to claim 1; wherein
Ar$^1$ represents aryl which is unsubstituted, or mono-, di-, or tri-substituted, wherein the substituents are independently selected from the group consisting of (C$_{1-4}$)alkyl, (C$_{1-4}$)alkoxy, halogen, (C$_{1-3}$)fluoroalkyl, (C$_{1-3}$)fluoroalkoxy, (C$_{1-3}$)fluoroalkyl-thio-, and (C$_{3-6}$)cycloalkyl-(C$_{1-4}$)alkoxy; or
Ar$^1$ represents heteroaryl which is unsubstituted, or mono-, di-, or tri-substituted, wherein the substituents are independently selected from the group consisting of (C$_{1-4}$) alkyl, (C$_{1-4}$)alkoxy and (C$_{1-3}$)fluoroalkyl;
in a free or a pharmaceutically acceptable salt.
4. The compound according to claim 1; wherein, in case Ar$^1$ represents aryl, said aryl is
phenyl which is unsubstituted, or mono-, di-, or tri-substituted, wherein the substituents are independently selected from the group consisting of (C$_{1-4}$)alkyl, (C$_{1-4}$) alkoxy, halogen, (C$_{1-3}$)fluoroalkyl, (C$_{1-3}$)fluoroalkoxy, (C$_{1-3}$)fluoroalkyl-thio-, and (C$_{3-6}$)cycloalkyl-(C$_{1-4}$) alkoxy; or
naphthyl which is unsubstituted, or mono-, or di-substituted, wherein the substituents are independently selected from the group consisting of (C$_{1-4}$)alkyl, (C$_{1-4}$) alkoxy, halogen, (C$_{1-3}$)fluoroalkyl, and (C$_{1-3}$)fluoroalkoxy; or
a phenyl ring fused to a 5- or 6-membered saturated or partially unsaturated non-aromatic ring optionally containing 1 to 2 oxygen atoms which is unsubstituted, or mono-, or di-substituted wherein the substituents are independently selected from the group consisting of methyl, methoxy, and halogen;
in a free or a pharmaceutically acceptable salt.
5. The compound according to claim 1; wherein Z represents a O; in a free or a pharmaceutically acceptable salt.

6. The compound according to claim 1; wherein
   $Ar^3$ represents phenyl which is unsubstituted, or mono-, di-, or tri-substituted wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy; or
   $Ar^3$ represents 5- to 6-membered heteroaryl which is unsubstituted, or mono-, di-, or tri-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy;
in a free or a pharmaceutically acceptable salt.

7. The compound according to claim 1; wherein $R^3$ represents
   phenyl which is mono-, or di-substituted, wherein one substituent is $(C_{1-4})$alkoxy, or $(C_{1-3})$fluoroalkoxy in position 4 of said phenyl and the other (if present) is selected from the group consisting of $(C_{1-4})$alkyl, $(C_{1-4})$alkoxy, halogen, $(C_{1-3})$fluoroalkyl, and $(C_{1-3})$fluoroalkoxy; or
   $Ar^3$—Z—$Ar^2$—* wherein the asterisk indicates the bond that is attached to the rest of the molecule; wherein
     $Ar^2$ represents phenyl or 6-membered heteroaryl which are substituted by Z and the rest of the molecule in a para arrangement,
     Z represents O, and
     $Ar^3$ represents phenyl or 5- to 6-membered heteroaryl wherein the phenyl or 5- to 6-membered heteroaryl is independently unsubstituted or mono-substituted, wherein the substituent is independently selected from the group consisting of $(C_{1-4})$alkyl, $(C_{1-4})$alkoxy, halogen, $(C_{1-3})$fluoroalkyl, and $(C_{1-3})$fluoroalkoxy;
in a free or a pharmaceutically acceptable salt.

8. The compound according to claim 1; wherein
   $R^4$ represents aryl which is mono-, di-, or tri-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, hydroxy-$(C_{1-4}$alkoxy, and $(C_{1-4})$alkoxy-$(C_{1-4})$alkoxy; wherein, in the specific case wherein said aryl is a bicyclic ring, the aryl may also be unsubstituted; or
   $R^4$ represents heteroaryl which is mono-, di-, or tri-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, hydroxy-$(C_{1-4})$ alkoxy, and $(C_{1-4})$alkoxy-$(C_{1-4})$alkoxy; wherein, in the specific case wherein said heteroaryl is a bicyclic ring, the heteroaryl may also be unsubstituted;
in a free or a pharmaceutically acceptable salt.

9. The compound according to claim 1; wherein, in case $R^4$ represents aryl, said aryl is
   phenyl which is mono-, di-, or tri-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, hydroxy-$(C_{1-4})$alkoxy, and $(C_{1-4})$alkoxy-$(C_{1-4})$alkoxy; or
   naphthyl which is unsubstituted, or mono-, or di-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy; or
   a phenyl ring fused to a 5- or 6-membered saturated or partially unsaturated non-aromatic ring optionally containing 1 to 2 oxygen atoms which is unsubstituted, or mono-, or di-substituted wherein the substituents are independently selected from the group consisting of methyl, methoxy, and halogen;
in a free or a pharmaceutically acceptable salt.

10. A compound of formula (II)

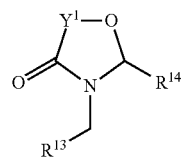

Formula (II)

wherein
$Y^1$ represents $CH_2$, $CH(CH_3)$ or $CH(CH_3)_2$;

$R^{13}$ represents

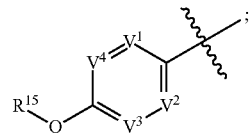

wherein
$R^{15}$ represents $(C_{1-4})$alkyl or $(C_{1-3})$fluoroalkyl;
   $V^1$, $V^2$ and $V^4$ are CH, and $V^3$ is $CR^{17}$, wherein optionally one or two of $V^1$, $V^2$, $V^3$ and V4 may also be N; and
   $R^{17}$ is hydrogen or halogen; or
$R^{15}$ represents phenyl or 5- to 6-membered heteroaryl, wherein the phenyl or 5- to 6-membered heteroaryl is independently unsubstituted, or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy; and
   one or two of $V^1$, $V^2$, $V^3$ and $V^4$ are CH or N and the remaining are CH; and $R^{14}$ represents a group selected from the group consisting of:

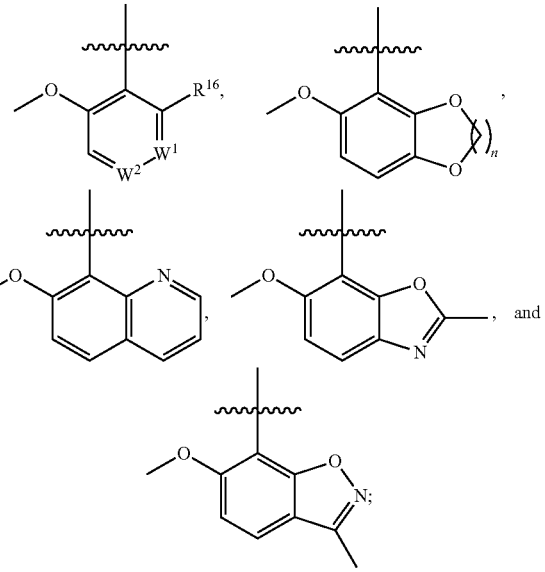

wherein
W¹ represents CH and W² represents CR¹⁷ or N, or
W¹ represents N and W² represents CH;
R¹⁶ represents methyl, $(C_{1-3})$alkoxy, halogen, $(C_{1-2})$ fluoroalkoxy, or trifluoromethyl;
R¹⁷ represents hydrogen, methyl or fluoro; and
n represents the integer 1 or 2;
in a free or a pharmaceutically acceptable salt.

11. The compound according to claim 1 selected from the group consisting of:
3-(4-Chloro-3-trifluoromethyl-benzyl)-2-(2-ethoxy-phenyl)-oxazolidin-4-one;
2-(2-Ethoxy-phenyl)-3-(2-methyl-benzyl)-oxazolidin-4-one;
2-(2-Ethoxy-phenyl)-3-(4-trifluoromethyl-benzyl)-oxazolidin-4-one;
2-(2-Ethoxy-phenyl)-3-(3-methoxy-benzyl)-oxazolidin-4-one;
2-(2-Ethoxy-phenyl)-3-(3-trifluoromethyl-benzyl)-oxazolidin-4-one;
2-(2-Ethoxy-phenyl)-3-(4-trifluoromethoxy-benzyl)-oxazolidin-4-one;
2-(2-Ethoxy-phenyl)-3-(3-trifluoromethoxy-benzyl)-oxazolidin-4-one;
2-(2-Ethoxy-phenyl)-3-(4-fluoro-3-methyl-benzyl)-oxazolidin-4-one;
3-(3-Chloro-4-fluoro-benzyl)-2-(2-ethoxy-phenyl)-oxazolidin-4-one;
3-(3-Chloro-2-fluoro-5-trifluoromethyl-benzyl)-2-(2-ethoxy-phenyl)-oxazolidin-4-one;
2-(2-Ethoxy-phenyl)-3-(2-methyl-3-trifluoromethyl-benzyl)-oxazolidin-4-one;
3-(2-Chloro-5-trifluoromethyl-benzyl)-2-(2-ethoxy-phenyl)-oxazolidin-4-one;
2-(2-Ethoxy-phenyl)-3-(2-fluoro-5-trifluoromethyl-benzyl)-oxazolidin-4-one;
2-(2-Ethoxy-phenyl)-3-(4-fluoro-3-trifluoromethyl-benzyl)-oxazolidin-4-one;
2-(2-Ethoxy-phenyl)-3-(3-fluoro-4-trifluoromethyl-benzyl)-oxazolidin-4-one;
3-(2-Chloro-3,6-difluoro-benzyl)-2-(2-ethoxy-phenyl)-oxazolidin-4-one;
3-(4-Chloro-3-fluoro-benzyl)-2-(2-ethoxy-phenyl)-oxazolidin-4-one;
3-(3-Chloro-4-trifluoromethoxy-benzyl)-2-(2-ethoxy-phenyl)-oxazolidin-4-one;
3-(4-Chloro-2-fluoro-benzyl)-2-(2-ethoxy-phenyl)-oxazolidin-4-one;
2-(2-Ethoxy-phenyl)-3-(2-fluoro-benzyl)-oxazolidin-4-one;
3-(4-Chloro-benzyl)-2-(2-ethoxy-phenyl)-oxazolidin-4-one;
2-(2-Ethoxy-phenyl)-3-(2-fluoro-4-trifluoromethyl-benzyl)-oxazolidin-4-one;
3-(2,6-Dichloro-benzyl)-2-(2-ethoxy-phenyl)-oxazolidin-4-one;
2-(2-Ethoxy-phenyl)-3-(3-methyl-benzyl)-oxazolidin-4-one;
2-(2-Ethoxy-phenyl)-3-(4-fluoro-benzyl)-oxazolidin-4-one;
3-(3,4-Difluoro-benzyl)-2-(2-ethoxy-phenyl)-oxazolidin-4-one;
2-(2-Ethoxy-phenyl)-3-(4-methoxy-benzyl)-oxazolidin-4-one;
2-(2-Ethoxy-phenyl)-3-(2-methyl-5-trifluoromethyl-benzyl)-oxazolidin-4-one;
3-(3,4-Dichloro-benzyl)-2-(2-ethoxy-phenyl)-oxazolidin-4-one;
3-(2,4-Dichloro-benzyl)-2-(2-ethoxy-phenyl)-oxazolidin-4-one;
3-(3-Chloro-4-methyl-benzyl)-2-(2-ethoxy-phenyl)-oxazolidin-4-one;
2-(2,6-Dimethoxy-phenyl)-3-(4-trifluoromethyl-benzyl)-oxazolidin-4-one;
2-(2,6-Dimethoxy-phenyl)-3-(2-trifluoromethoxy-benzyl)-oxazolidin-4-one;
2-(2,6-Dimethoxy-phenyl)-3-(4-trifluoromethoxy-benzyl)-oxazolidin-4-one;
2-(2,6-Dimethoxy-phenyl)-3-(3-trifluoromethoxy-benzyl)-oxazolidin-4-one;
3-(3-Chloro-4-fluoro-benzyl)-2-(2,6-dimethoxy-phenyl)-oxazolidin-4-one;
3-(3-Chloro-2-fluoro-5-trifluoromethyl-benzyl)-2-(2,6-dimethoxy-phenyl)-oxazolidin-4-one;
2-(2,6-Dimethoxy-phenyl)-3-(4-fluoro-3-trifluoromethyl-benzyl)-oxazolidin-4-one;
3-(4-Chloro-3-fluoro-benzyl)-2-(2,6-dimethoxy-phenyl)-oxazolidin-4-one;
3-(3-Chloro-4-trifluoromethoxy-benzyl)-2-(2,6-dimethoxy-phenyl)-oxazolidin-4-one;
2-(2,6-Dimethoxy-phenyl)-3-(2,4,6-trimethyl-benzyl)-oxazolidin-4-one;
3-(2,4-Dichloro-benzyl)-2-(2,6-dimethoxy-phenyl)-oxazolidin-4-one;
3-(3-Chloro-4-methyl-benzyl)-2-(2,6-dimethoxy-phenyl)-oxazolidin-4-one;
2-(2,6-Dimethoxy-phenyl)-3-(2,6-dimethyl-benzyl)-oxazolidin-4-one;
3-(2-Chloro-benzyl)-2-(2-ethoxy-phenyl)-oxazolidin-4-one;
3-(2,5-Dichloro-benzyl)-2-(2-ethoxy-phenyl)-oxazolidin-4-one;
2-(2,6-Dimethoxy-phenyl)-3-(4-phenoxy-benzyl)-oxazolidin-4-one;
2-(2,6-Dimethoxy-phenyl)-3-(3-fluoro-4-trifluoromethoxy-benzyl)-oxazolidin-4-one;
3-(4-Difluoromethoxy-benzyl)-2-(2,6-dimethoxy-phenyl)-oxazolidin-4-one;
2-(2,6-Dimethoxy-phenyl)-5,5-dimethyl-3-(4-phenoxy-benzyl)-oxazolidin-4-one;
2-(2,6-Dimethoxy-phenyl)-(R)-5-methyl-3-(4-phenoxy-benzyl)-oxazolidin-4-one;
3-(4-Difluoromethoxy-benzyl)-2-(2,6-dimethoxy-phenyl)-(R)-5-methyl-oxazolidin-4-one;
2-(2,6-Dimethoxy-phenyl)-(R)-5-methyl-3-naphthalen-2-ylmethyl-oxazolidin-4-one;
2-(2,6-Dimethoxy-phenyl)-3-(4-propoxy-benzyl)-oxazolidin-4-one;
2-(2,6-Dimethoxy-phenyl)-3-(3-fluoro-4-trifluoromethoxy-benzyl)-(R)-5-methyl-oxazolidin-4-one;
3-(3-Chloro-4-trifluoromethoxy-benzyl)-2-(2,6-dimethoxy-phenyl)-(R)-5-methyl-oxazolidin-4-one;
2-(2,6-Dimethoxy-phenyl)-5,5-dimethyl-3-naphthalen-2-ylmethyl-oxazolidin-4-one;
3-(3-Chloro-4-trifluoromethoxy-benzyl)-2-(2,6-dimethoxy-phenyl)-5,5-dimethyl-oxazolidin-4-one;
2-(2,6-Dimethoxy-phenyl)-(S)-5-methyl-3-(4-phenoxy-benzyl)-oxazolidin-4-one;
2-(2,6-Dimethoxy-phenyl)-3-(4-isopropoxy-benzyl)-oxazolidin-4-one;
2-(2,6-Dimethoxy-phenyl)-5,5-dimethyl-3-(4-trifluoromethoxy-benzyl)-oxazolidin-4-one;

3   -Benzothiazol-2-ylmethyl-2-(2,6-dimethoxy-phenyl)-(R)-5-methyl-oxazolidin-4-one;
2-(2,6-Dimethoxy-phenyl)-(R)-5-methyl-3-(4-trifluoromethoxy-benzyl)-oxazolidin-4-one;
3 -Benzothiazol-2-ylmethyl-2-(2,6-dimethoxy-phenyl)-5, 5-dimethyl-oxazolidin-4-one;
3-(4-Cyclopropylmethoxy-benzyl)-2-(2,6-dimethoxy-phenyl)-oxazolidin-4-one;
2-(2,6-Dimethoxy-phenyl)-(S)-5-methyl-3-naphthalen-2-ylmethyl-oxazolidin-4-one;
2-(2,6-Dimethoxy-phenyl)-3-(3-fluoro-4-trifluoromethoxy-benzyl)-5,5-dimethyl-oxazolidin-4-one;
3 -Benzooxazol-2-ylmethyl-2-(2,6-dimethoxy-phenyl)-5, 5-dimethyl-oxazolidin-4-one;
3   -(4-Difluoromethoxy-benzyl)-2-(2,6-dimethoxy-phenyl)-5 ,5 -dimethyl-oxazolidin-4-one;
2-(2,6-Dimethoxy-phenyl)-5 ,5 -dimethyl-3 -(1-methyl-1H-benzoimidazol-2-ylmethyl)-oxazolidin-4-one;
3 -Benzo [1,3]dioxol-5 -ylmethyl-2-(2,6-dimethoxy-phenyl)-5 ,5 -dimethyl-oxazolidin-4-one;
2-(2,6-Dimethoxy-phenyl)-3-(4-methoxy-benzyl)-5,5-dimethyl-oxazolidin-4-one;
(R)-2-(2,6-Dimethoxy-phenyl)-5-methyl-3-(4-propoxy-benzyl)-oxazolidin-4-one;
2-(2,6-Dimethoxy-phenyl)-3-(4-isopropoxy-benzyl)-(R)-5-methyl-oxazolidin-4-one;
3   -(4-Cyclopropylmethoxy-benzyl)-2-(2,6-dimethoxy-phenyl)-(R)-5 -methyl-oxazolidin-4-one;
2-(2,6-Dimethoxy-phenyl)-3-(4-isopropoxy-benzyl)-5,5-dimethyl-oxazolidin-4-one;
2-(2,6-Dimethoxy-phenyl)-5,5-dimethyl-3-(4-propoxy-benzyl)-oxazolidin-4-one;
3   -(4-Cyclopropylmethoxy-benzyl)-2-(2,6-dimethoxy-phenyl)-5 ,5 -dimethyl-oxazolidin-4-one;
2-(2,6-Dimethoxy-phenyl)-3-(4-ethoxy-benzyl)-(R)-5-methyl-oxazolidin-4-one;
2-(2,6-Dimethoxy-phenyl)-3-(4-ethoxy-benzyl)-5,5-dimethyl-oxazolidin-4-one;
3   -(3   -Chloro-4-trifluoromethoxy-benzyl)-2-(2,6-dimethyl-phenyl)-5 ,5 -dimethyl-oxazolidin-4-one;
3   -(3   -Chloro-4-trifluoromethoxy-benzyl)-2-(2,6-difluoro-phenyl)-5 ,5 -dimethyl-oxazolidin-4-one;
3 -(3 -Chloro-4-trifluoromethoxy-benzyl)-2-(2-methoxy-6-methyl-phenyl)-5 ,5 -dimethyl-oxazolidin-4-one;
2-(2-Fluoro-6-methoxy-phenyl)-5,5-dimethyl-3-(4-phenoxy-benzyl)-oxazolidin-4-one;
2-(2-Chloro-6-methoxy-phenyl)-5,5-dimethyl-3-(4-phenoxy-benzyl)-oxazolidin-4-one;
2-(2-Methoxy-6-trifluoromethyl-phenyl)-5,5-dimethyl-3-(4-phenoxy-benzyl)-oxazolidin-4-one;
3   -Biphenyl-4-ylmethyl-2-(2,6-dimethoxy-phenyl)-5 ,5 -dimethyl-oxazolidin-4-one;
2-(2,6-Dimethoxy-phenyl)-5,5-dimethyl-3-(4-trifluoromethylsulfanyl-benzyl)-oxazolidin-4-one;
2-(2,6-Dimethoxy-phenyl)-5,5-dimethyl-3-(6-phenoxy-pyridin-3-ylmethyl)-oxazolidin-4-one;
2-(2,6-Dimethoxy-phenyl)-5 ,5 -dimethyl-3 -(5-phenoxy-pyridin-2-ylmethyl)-oxazolidin-4-one;
2-(2,6-Dimethoxy-phenyl)-5,5-dimethyl-3-[4-(pyridin-2-yloxy)-benzyl]-oxazolidin-4-one;
2-(2,6-Dimethoxy-phenyl)-5,5-dimethyl-3-[4-(pyrazin-2-yloxy)-benzyl]-oxazolidin-4-one;
2-(2,6-Dimethoxy-phenyl)-5 ,5-dimethyl-3-[4-(6-methyl-pyridazin-3-yloxy)-benzyl]-oxazolidin-4-one;
2-(2,6-Dimethoxy-phenyl)-5,5-dimethyl-3-[4-(thiazol-2-yloxy)-benzyl]-oxazolidin-4-one;
2-(2,6-Dimethoxy-phenyl)-5,5-dimethyl-3-[4-(pyrimidin-2-yloxy)-benzyl]-oxazolidin-4-one;
2-(2-Isopropoxy-6-methoxy-phenyl)-5,5-dimethyl-3-(4-phenoxy-benzyl)-oxazolidin-4-one;
2-(2-Ethoxy-6-methoxy-phenyl)-5,5-dimethyl-3-(4-phenoxy-benzyl)-oxazolidin-4-one;
2-[2-Methoxy-6-(2-methoxy-ethoxy)-phenyl]-5,5-dimethyl-3-(4-phenoxy-benzyl)-oxazolidin-4-one; and
2-[2-(3-Hydroxy-propoxy)-6-methoxy-phenyl]-5,5-dimethyl-3-(4-phenoxy-benzyl)-oxazolidin-4-one;
in a free or a pharmaceutically acceptable salt.

12. The pharmaceutical composition containing, as active principle, the compound according to claim 1, or a pharmaceutically acceptable salt thereof, and at least one therapeutically inert excipient.

13. A method for the treatment of a disease or disorder wherein the compound of claim 1 is administered to a patient in need therof, wherein said disease or disorder is an insomnia.

14. A method for the treatment of a disease or disorder wherein the compound of claim 10 is administered to a patient in need thereof, wherein said disease or disorder is an insomnia.

15. A pharmaceutical composition comprising a compound according to claim 10, in a free or pharmaceutically acceptable salt form, and a pharmaceutically acceptable carrier.

* * * * *